(12) United States Patent
Oshima

(10) Patent No.: US 12,220,164 B2
(45) Date of Patent: Feb. 11, 2025

(54) TREATMENT SYSTEM AND IMAGE GENERATION METHOD

(71) Applicant: ASAHI INTECC CO., LTD., Seto (JP)

(72) Inventor: Fumiyoshi Oshima, Seto (JP)

(73) Assignee: ASAHI INTECC CO., LTD., Seto (JP)

(*) Notice: Subject to any disclaimer, the term of this patent is extended or adjusted under 35 U.S.C. 154(b) by 931 days.

(21) Appl. No.: 17/321,995

(22) Filed: May 17, 2021

(65) Prior Publication Data
US 2021/0267678 A1  Sep. 2, 2021

Related U.S. Application Data

(63) Continuation of application No. PCT/JP2019/047014, filed on Dec. 2, 2019.

(30) Foreign Application Priority Data

Dec. 3, 2018 (JP) ................. 2018-226287

(51) Int. Cl.
*A61B 5/05* (2021.01)
*A61B 18/14* (2006.01)
(Continued)

(52) U.S. Cl.
CPC .......... *A61B 18/1492* (2013.01); *A61B 90/36* (2016.02); *A61B 5/0215* (2013.01);
(Continued)

(58) Field of Classification Search
CPC ......... A61B 5/242; A61B 5/243; A61B 5/339; A61B 5/336; A61B 5/0515; A61B 5/05;
(Continued)

(56) References Cited

U.S. PATENT DOCUMENTS 6,230,037 B1   5/2001  Tsukada et al.
7,742,806 B2   6/2010  Sternickel et al.
(Continued)

FOREIGN PATENT DOCUMENTS

CN   104739411 A   7/2015
EP   0 750 520 B1  8/2000
(Continued)

OTHER PUBLICATIONS

Werner Moshage et al., "Biomagnetic Localization of Ventricular Arrhythmias", Radiology, Radiological Society of North America, Inc, US, vol. 180, No. 3, pp. 685-692, Sep. 1, 1991.
(Continued)

*Primary Examiner* — Joel F Brutus
(74) *Attorney, Agent, or Firm* — Oliff PLC

(57) ABSTRACT

A treatment system includes a magnetic sensor configured to detect a biomagnetic field generated by a living body to be treated, a catheter configured to be inserted into the living body, an image information processor programmed to generate a combined image including a first image expressing a strength of the biomagnetic field and a second image expressing a position of the catheter, by using biomagnetic field information output from the magnetic sensor and position information of the catheter inserted into the living body, and a display configured to display the combined image.

20 Claims, 18 Drawing Sheets

(51) Int. Cl.
| | |
|---|---|
| *A61B 90/00* | (2016.01) |
| *A61B 5/00* | (2006.01) |
| *A61B 5/0215* | (2006.01) |
| *A61B 5/0265* | (2006.01) |
| *A61B 5/0275* | (2006.01) |
| *A61B 5/0515* | (2021.01) |
| *A61B 5/06* | (2006.01) |
| *A61B 5/1473* | (2006.01) |
| *A61B 5/24* | (2021.01) |
| *A61B 5/242* | (2021.01) |
| *A61B 5/243* | (2021.01) |
| *A61B 5/336* | (2021.01) |
| *A61B 5/339* | (2021.01) |
| *A61B 18/00* | (2006.01) |
| *A61B 18/02* | (2006.01) |
| *A61B 18/12* | (2006.01) |
| *A61B 18/24* | (2006.01) |
| *A61B 34/10* | (2016.01) |
| *A61B 34/20* | (2016.01) |
| *G01R 33/02* | (2006.01) |
| *G01R 33/035* | (2006.01) |

(52) U.S. Cl.
CPC ........... *A61B 5/0265* (2013.01); *A61B 5/0275* (2013.01); *A61B 5/05* (2013.01); *A61B 5/0515* (2013.01); *A61B 5/06* (2013.01); *A61B 5/062* (2013.01); *A61B 5/1473* (2013.01); *A61B 5/24* (2021.01); *A61B 5/242* (2021.01); *A61B 5/243* (2021.01); *A61B 5/336* (2021.01); *A61B 5/339* (2021.01); *A61B 5/68* (2013.01); *A61B 5/6846* (2013.01); *A61B 5/6869* (2013.01); *A61B 2018/00351* (2013.01); *A61B 2018/00636* (2013.01); *A61B 2018/00773* (2013.01); *A61B 2018/0231* (2013.01); *A61B 18/1206* (2013.01); *A61B 18/14* (2013.01); *A61B 18/24* (2013.01); *A61B 2034/101* (2016.02); *A61B 2034/102* (2016.02); *A61B 2034/2051* (2016.02); *A61B 2090/0815* (2016.02); *A61B 2090/364* (2016.02); *A61B 2090/367* (2016.02); *A61B 2090/368* (2016.02); *A61B 90/39* (2016.02); *A61B 2090/3912* (2016.02); *A61B 2090/3954* (2016.02); *G01R 33/02* (2013.01); *G01R 33/035* (2013.01)

(58) Field of Classification Search
CPC ........... A61B 5/06; A61B 5/1473; A61B 5/68; A61B 5/062; A61B 2090/3912; A61B 2090/3954; A61B 2090/0815; A61B 2090/364; A61B 2090/367
See application file for complete search history.

(56) References Cited

U.S. PATENT DOCUMENTS

| | | |
|---|---|---|
| 9,433,363 B1 | 9/2016 | Erasala et al. |
| 2008/0033312 A1 | 2/2008 | Nakai et al. |
| 2014/0257080 A1* | 9/2014 | Dunbar .................. A61B 5/062 |
| | | 600/409 |
| 2019/0133477 A1 | 5/2019 | Kawabata et al. |

FOREIGN PATENT DOCUMENTS

| | | |
|---|---|---|
| JP | 2001-87236 A | 4/2001 |
| JP | 2011-229808 A | 11/2011 |
| WO | 2005/117695 A1 | 12/2005 |
| WO | 2017/209273 A1 | 12/2017 |

OTHER PUBLICATIONS

Gronros K. et al, "Magnetocardiographic Localization of a Non-Magnetic Pacing Catheter", Engineering in Medicine and Biology Society, 1996. Bridging Disciplines for Biomedicine., 18th Annual International Conference of the IEEE Amsterdam, Netherlands Oct. 31, 1996-Nov. 3, 1996, New York, NY, USA, IEEE, US, vol. 4, pp. 1429-1430, XP010262063, DOI: 10.1109/IEMBS. 1996.647489 ISBN: 978-0-7803-3811-1, Oct. 31, 1996.

* cited by examiner

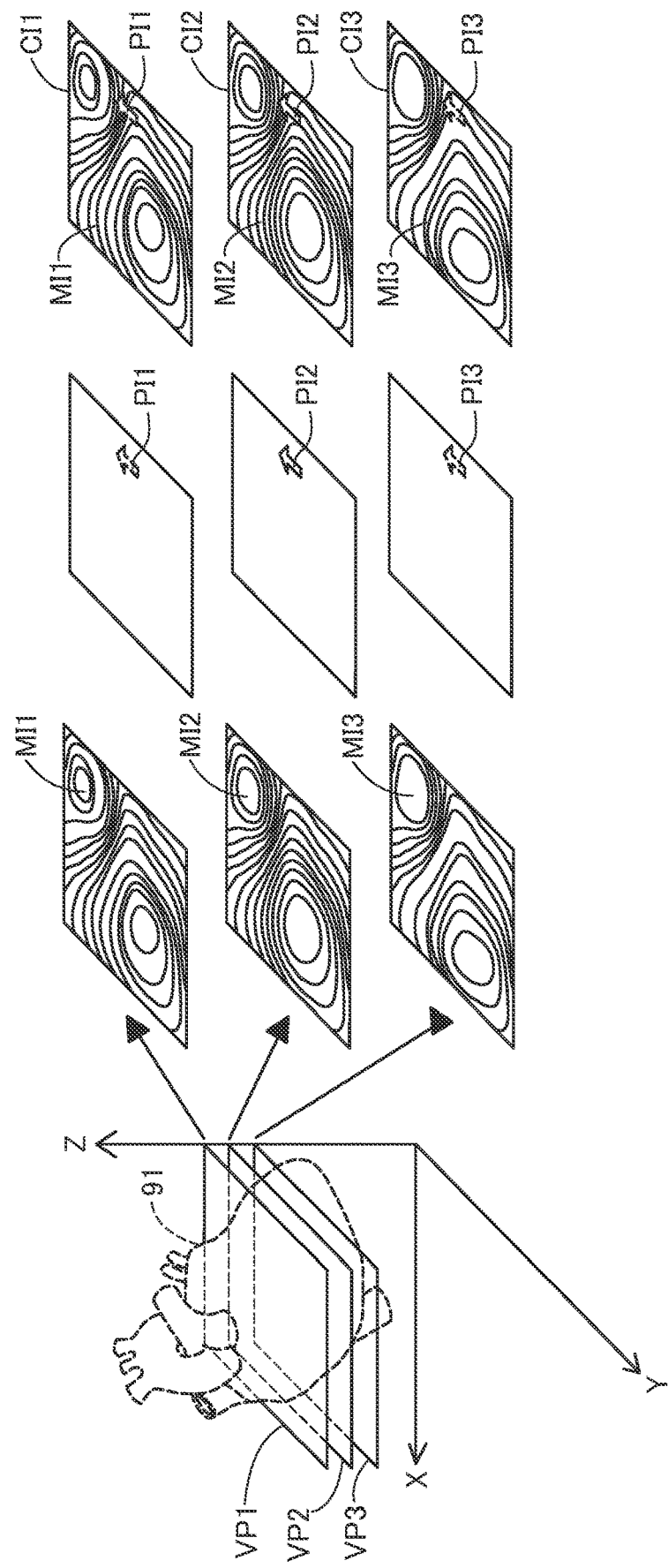

TREATMENT SYSTEM AND IMAGE GENERATION METHOD

CROSS REFERENCE TO RELATED APPLICATIONS

The present application is a Bypass Continuation of PCT/JP2019/047014, filed Dec. 2, 2019, which is based upon and claims priority from Japanese Application No. 2018-226287 filed on Dec. 3, 2018, the entirety of the prior applications being hereby incorporated by reference into this application.

TECHNICAL FIELD

The disclosed embodiments relate to a treatment system and an image generation method.

BACKGROUND ART

Conventionally, magnetic sensors for detecting biomagnetic fields generated by living bodies such as a human body are known. For example, Patent Literature 1 and 2 disclose a biomagnetic measurement device including a magnetic sensor that detects a biomagnetic field generated by a human body. Further, Patent Literature 3 discloses a magnetocardiogram in which a biomagnetic field is visualized. Moreover, Patent Literature 4 discloses a current density map of a heart.

CITATION LIST

Patent Literature

Patent Literature 1: International Patent Application No. 2017/209273
Patent Literature 2: International Patent Application No. 2005/117695
Patent Literature 3: U.S. Pat. No. 7,742,806
Patent Literature 4: U.S. Pat. No. 9,433,363

SUMMARY

In an arrhythmia treatment, an improvement in the convenience of a treatment system for performing treatment while confirming a biomagnetic field generated by a human body to be treated is desired, for example. However, even when using the above-mentioned prior art, there is still room for improvement in the convenience of the treatment system.

The disclosed embodiments have been made to solve the problems described above, and an object thereof is to provide a technique for improving the convenience of a treatment system.

The disclosed embodiments have been made to solve at least some of the above-described problems, and can be implemented as the following aspects.

(1) According to one aspect of the disclosed embodiments, a treatment system is provided. This treatment system includes a magnetic sensor that detects a biomagnetic field generated by a living body to be treated, a catheter to be inserted into the living body, an image information processing portion that generates a combined image including an image expressing a strength of the biomagnetic field and an image expressing a position of the catheter, by using biomagnetic field information output from the magnetic sensor and position information of the catheter inserted into the living body, and a display portion that displays the combined image.

According to this configuration, an operator of the catheter can perform treatment while confirming a combined image including an image expressing the strength of the biomagnetic field and an image expressing the position of the catheter, and thus, it is possible to improve the convenience during treatment.

(2) In the treatment system of the above-described aspect, the image information processing portion may generate a combined image including an image expressing a biomagnetic field distribution being a distribution of a biomagnetic field generated by a specific organ of the living body, and an image indicating a position of a distal end portion of the catheter relative to the biomagnetic field distribution. According to this configuration, by using the displayed combined image, an operator of the catheter can easily confirm a position of a distal end portion of the catheter relative to a biomagnetic field distribution of a specific organ, and thus, it is possible to further improve the convenience during treatment.

(3) In the treatment system of the above-described aspect, the image information processing portion may generate a combined image including an image expressing the biomagnetic field distribution and an image indicating a position and an orientation of the distal end portion of the catheter relative to the biomagnetic field distribution. According to this configuration, an operator of the catheter can easily confirm the position and orientation of the distal end portion of the catheter relative to a biomagnetic field distribution of a specific organ, and thus, it is possible to further improve the convenience during treatment.

(4) In the treatment system of the above-described aspect, the display portion may display two of the combined images, and the two combined images displayed on the display portion may include an image expressing the biomagnetic field distribution at different positions of the specific organ and an image indicating a position of the distal end portion of the catheter relative to each of the biomagnetic field distributions. According to this configuration, an operator of the catheter can confirm the biomagnetic field distribution at different positions of a specific organ and a relative position of the distal end portion of the catheter, and thus, it is possible to further improve the convenience during treatment.

(5) The treatment system of the above-described aspect may further include an operating portion that changes a content of the combined image displayed on the display portion, and if the operating portion is operated, the image information processing portion may use the biomagnetic field information to generate a new combined image including an image expressing a biomagnetic field distribution at a position of the biomagnetic field generated by the specific organ corresponding to an operation of the operating portion and an image indicating a position of the distal end portion of the catheter relative to the biomagnetic field distribution. According to this configuration, an operator of the catheter can confirm the biomagnetic field distribution at a desired position of the specific organ and a relative position of the distal end portion of the catheter, by operating the operating portion, and thus, it is possible to further improve the convenience during treatment.

(6) In the treatment system of the above-described aspect, the catheter may include a marker at a distal end portion thereof, the magnetic sensor may also detect a magnetic field generated by the marker, and the image information processing processing portion may generate the combined image by using magnetic field information including position information of the marker output from the magnetic sensor and the biomagnetic field information. According to this configuration, it is possible to easily generate a combined image including an image expressing the strength of the biomagnetic field and an image expressing the position of the catheter, by using the magnetic field information including the position information of the marker.

The disclosed embodiments can be realized in various aspects, for example, in the form of an image generation device, an image generation method, an examination system, an examination method, a method of manufacturing a treatment system, a catheter used in a treatment system, and the like.

BRIEF DESCRIPTION OF DRAWINGS

FIG. 8 is a schematic diagram for describing a method of generating a combined image.

DETAILED DESCRIPTION OF EMBODIMENTS

First Embodiment

Figure 1:
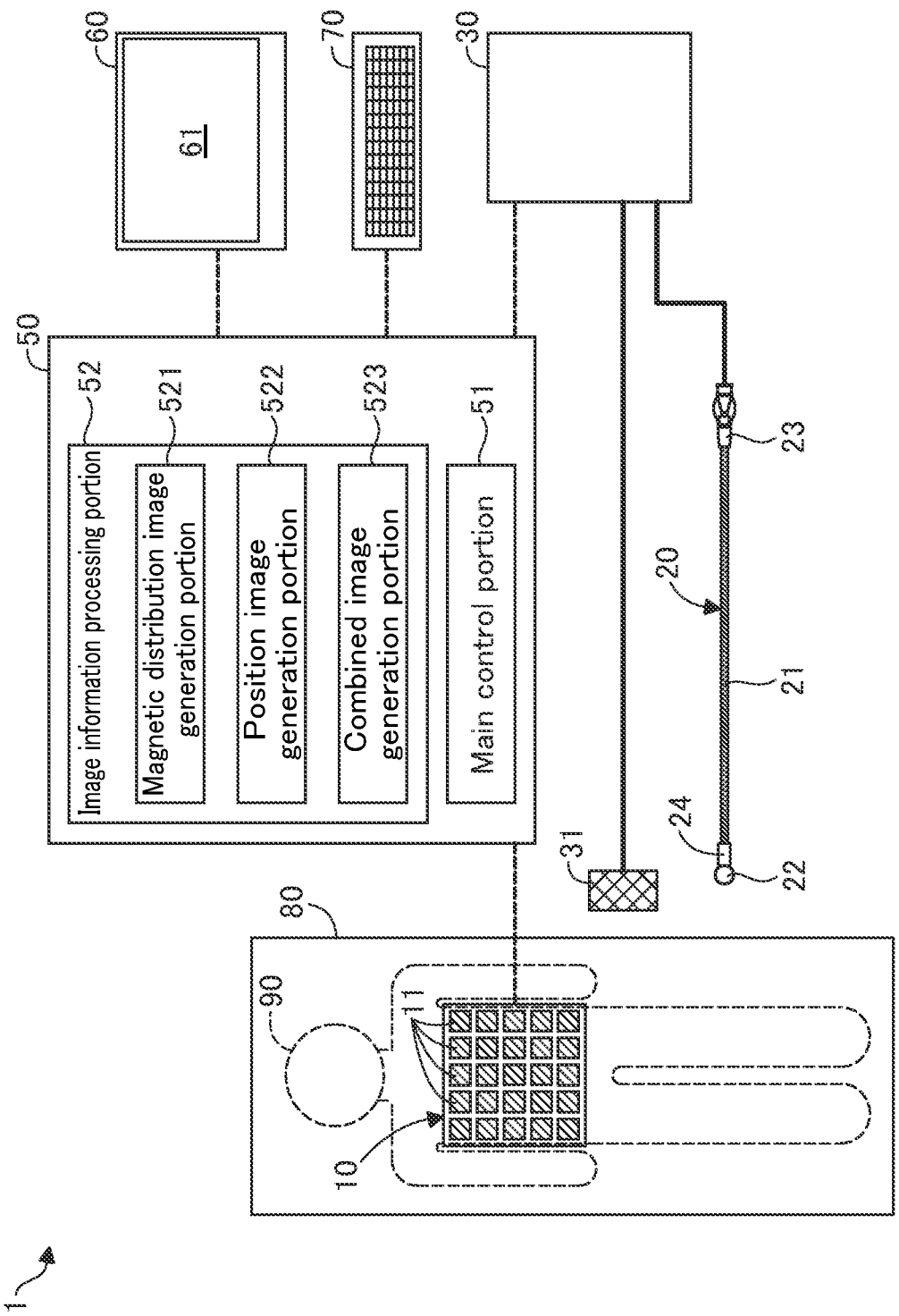
FIG. 1 is an explanatory diagram illustrating a simplified configuration of a treatment system of a first embodiment.

FIG. 1 is an explanatory diagram illustrating a simplified configuration of a treatment system 1 of a first embodiment. The treatment system 1 is a device used for treating a living body (here, a human body) 90 to be treated, and includes a magnetic sensor array 10, a catheter 20, a high frequency generator 30, a computer 50, a monitor 60, and an operating portion 70. Here, as an example of the present embodiment, the treatment system 1 is described when used for an arrhythmia treatment.

The magnetic sensor array 10 is a device that detects a strength, an orientation, and the like of a biomagnetic field generated by the human body 90 to be treated, and in the magnetic sensor array 10, a plurality of magnetic sensors 11 are arranged are arranged vertically and horizontally to form a matrix. The magnetic sensor 11 is an element that detects the strength and orientation of a biomagnetic field, and examples thereof include a magnetoresistive effect element (MR), a magneto-impedance element (MI), and a superconducting quantum interference element (SQUID). Here, the magnetic sensor array 10 is arranged near a central portion of a table 80 on which the human body 90 lies during treatment. The magnetic sensor array 10 may be configured to be attached to the human body 90 during treatment. For example, the magnetic sensor array 10 may be formed in a band shape to be wound around the human body 90, or may be formed in a shape of a clothing item or a hat. In these cases, the magnetic sensors 11 can be arranged along the shape of the human body 90. Further, the magnetic sensor array 10 may be three-dimensionally arranged as the magnetic sensor arrays 10 on a plate on one side or both sides of a front surface and a rear surface of the human body 90 and on one side or both sides of both side surfaces of the human body. Here, an example of detecting the strength and orientation of a cardiac magnetic field generated by a heart 91 (FIG. 2), being one of organs of the human body 90, will be described.

Figure 2:
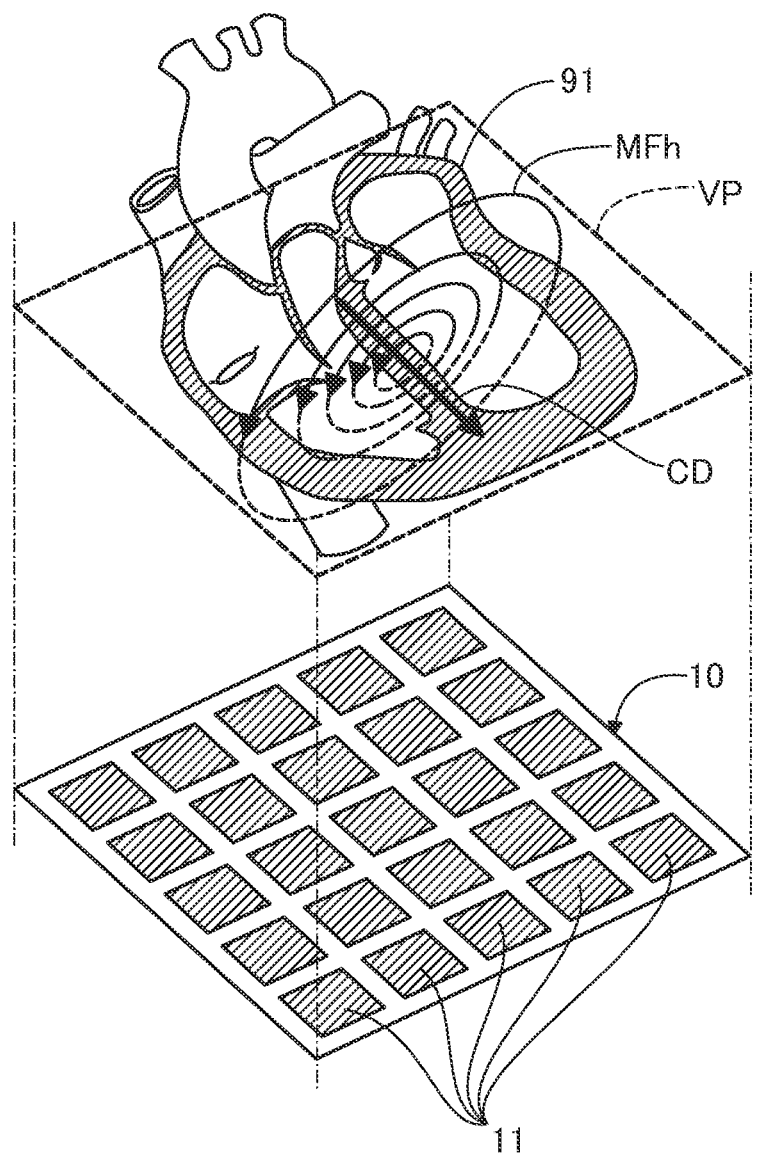
FIG. 2 is an explanatory diagram illustrating a method of detecting a biomagnetic field by a magnetic sensor array.

The catheter 20 is a so-called ablation catheter that is inserted into the human body 90 during treatment and generates a plasma from a distal end thereof inside the heart 91 (FIG. 2). The catheter 20 includes a main body portion 21, a distal tip 22, a connector 23, and a marker 24. The main body portion 21 has an oblong outer shape, and an unillustrated first wire (core wire) and a second wire having conductivity are arranged inside an electrically insulating outer layer of the main body portion 21. The distal tip 22 is provided at a distal end of the main body portion 21, and is electrically connected to a distal end of the first wire. The connector 23 is provided at the proximal end of the main body portion 21, and is connected to the high frequency generator 30. If the connector 23 and the high frequency generator 30 are connected, the proximal ends of the first wire and the second wire are electrically connected to the high frequency generator 30. The marker 24 is a conductive member used for detecting a position of a distal end portion of the catheter 20, and is provided on a distal end side of the main body portion 21, that is, on a proximal end side of the distal tip 22. Here, the marker 24 is electrically connected to a distal end of the second wire.

The high frequency generator 30 is a device that supplies a high frequency current to the catheter 20, supplies a high frequency current to the distal tip 22 via the first wire, and supplies a current for position detection to the marker 24 via the second wire. The high frequency generator 30 is also electrically connected to a current-carrying counter electrode plate 31, and supplies a high frequency current to the distal tip 22 to generate a plasma between the distal tip 22 and the current-carrying counter electrode plate 31. This plasma can be used to cauterize a portion of the heart 91 where arrhythmia occurs. The high frequency generator 30 supplies a current for position detection to the marker 24 to generate a magnetic field from the marker 24. Thus, the position and orientation of the distal end portion of the catheter 20 can be identified, which will be described later. Here, the high frequency generator 30 is connected to the computer 50 and, based on an instruction from the computer 50, switches a supply of a high frequency current to the distal tip 22 and a supply of a current for position detection to the marker 24 on and off.

The computer 50 is a device that controls the entire treatment system 1, and is electrically connected to each of the magnetic sensor array 10, the high frequency generator 30, the monitor 60, and the operating portion 70. The computer 50 includes a CPU, a ROM, and a RAM, which are not illustrated, and the CPU executes a program stored in the ROM to realize functions of a main control portion 51 and an image information processing portion 52.

The main control portion 51 exchanges pieces of information with the magnetic sensor array 10, the high frequency generator 30, the monitor 60, and the operating portion 70, to control the entire treatment system 1. When the operating portion 70 receives a predetermined operation, the main control portion 51 controls the high frequency generator 30 to supply a high frequency current to the distal tip 22. Further, when the main control portion 51 does not supply the high frequency current to the distal tip 22, the main control portion 51 intermittently supplies a current for position detection to the marker 24. The main control portion 51 acquires, from the magnetic sensor array 10, information about the strength and orientation of a biomagnetic field (hereinafter, also referred to as "first magnetic field information") detected by the magnetic sensor array 10 when the main control portion 51 does not supply a current to both of the distal tip 22 and the marker 24, and information about the strength and orientation of a magnetic field (hereinafter, also referred to as "second magnetic field information") detected by the magnetic sensor array 10 when the main control portion 51 supplies a detection current to the marker 24. The first magnetic field information is biomagnetic field information expressing the strength and orientation of a biomagnetic field MFh (FIG. 2) generated by the human body 90. The second magnetic field information is magnetic field information expressing the strength and orientation of a magnetic field (hereinafter, also referred to as "combined biomagnetic/marker magnetic field") in which both the biomagnetic field MFh generated by the human body 90 and a magnetic field (hereinafter, also referred to as "marker magnetic field") MFm (FIG. 5) generated by the marker 24 are combined. The second magnetic field information includes information about the marker magnetic field, and thus, it is possible to identify a position of the marker 24 inside the human body 90. Therefore, it can be said that the second magnetic field information includes position information of the catheter 20.

Figure 6A:
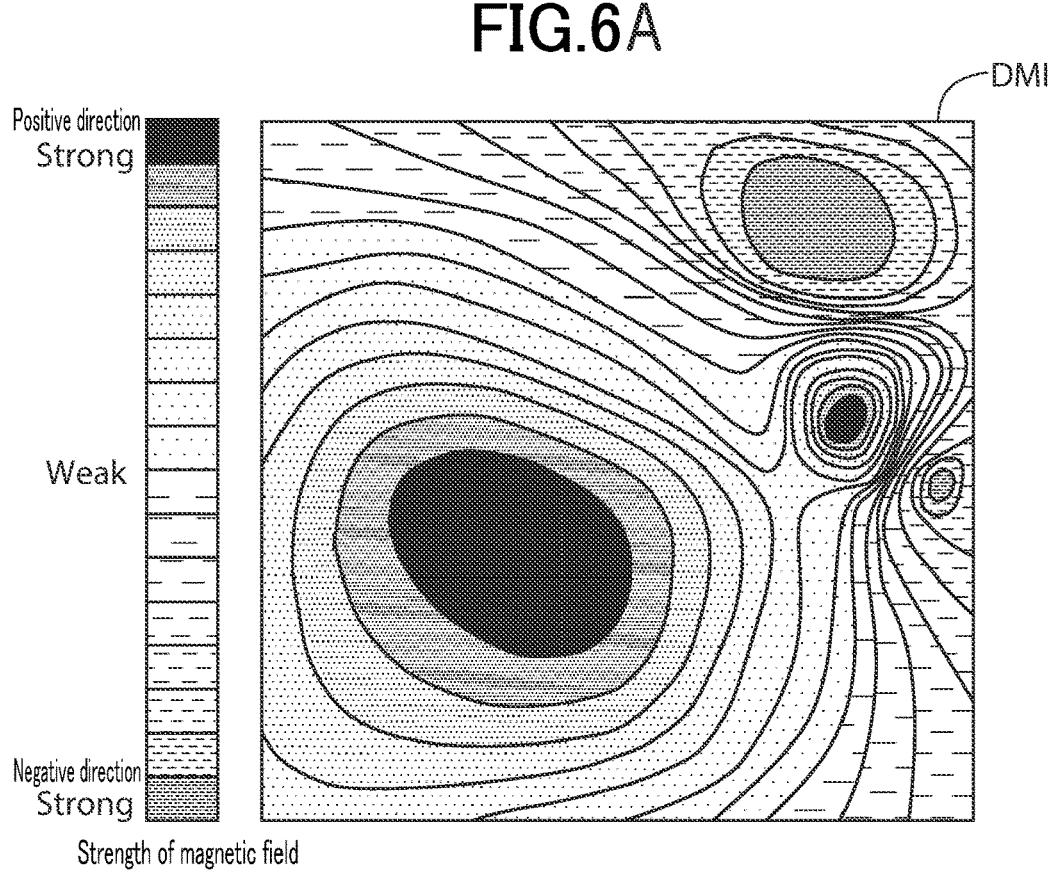
FIGS. 6A and 6B are diagrams for describing a catheter position image.
Figure 6B:
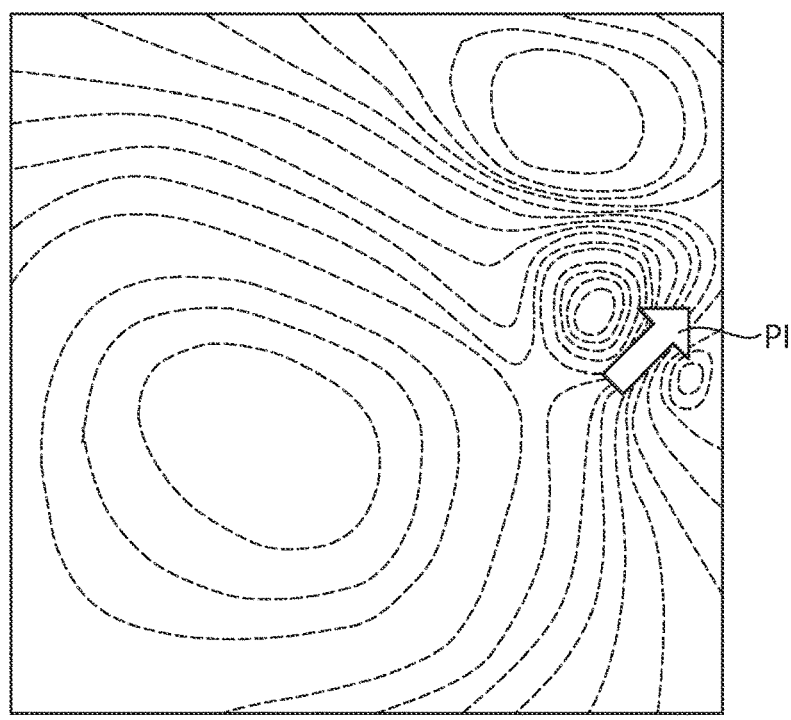

The image information processing portion 52 uses the first magnetic field information (biomagnetic field information) output from the magnetic sensor array 10 and the second magnetic field information (position information of the catheter 20) to generate a combined image CI described later. The image information processing portion 52 includes a magnetic distribution image generation portion 521, a position image generation portion 522, and a combined image generation portion 523. The magnetic distribution image generation portion 521 generates a magnetic field distribution image (magnetocardiogram) MI (FIG. 3B) from the first magnetic field information (biomagnetic field information). The position image generation portion 522 uses the second magnetic field information (position information of the catheter 20) to generate a catheter position image PI (FIG. 6B). The combined image generation portion 523 uses the biomagnetic field distribution image MI and the catheter position image PI to generate the combined image CI (for example, FIGS. 9A and 9B). A content of the biomagnetic field distribution image MI, the catheter position image PI, and the combined image CI will be described later. The generated combined image CI is displayed on a display screen 61 of the monitor 60 by the main control portion 51.

The monitor 60 is a display portion provided with the display screen 61, and includes a liquid crystal display or the like. The treatment system 1 may include a display portion other than the monitor 60. For example, the treatment system 1 may include smart glasses provided with a display screen, or may include a projector that projects an image. The operating portion 70 includes a keyboard or the like, and is operated, for example, when an operator of the catheter 20 switches a display content of the display screen 61. The operating portion 70 may be provided on a part of the catheter 20.

Figure 3A:
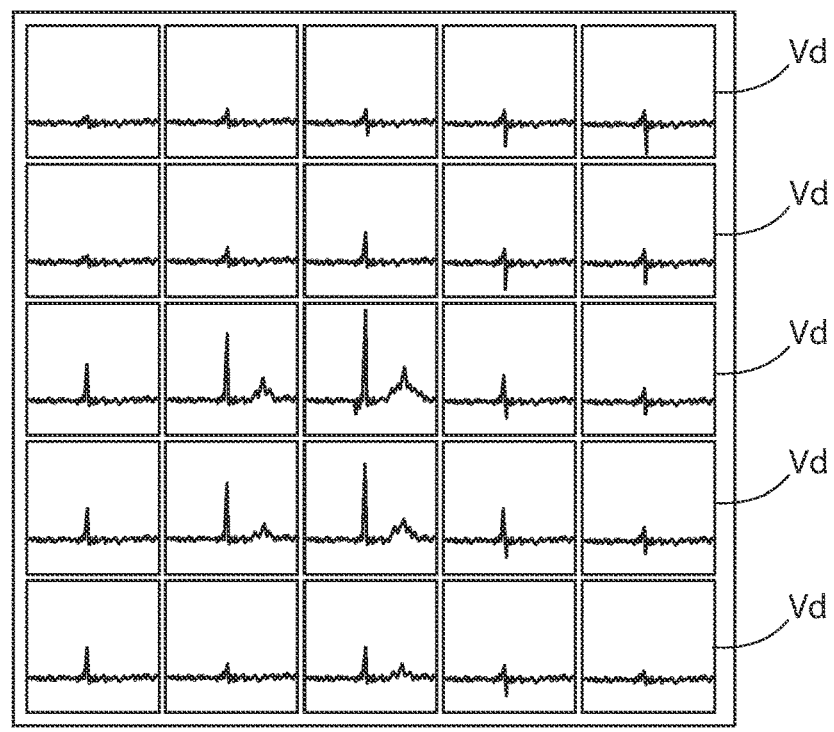
FIGS. 3A and 3B are diagrams for describing a biomagnetic field distribution image.
Figure 3B:
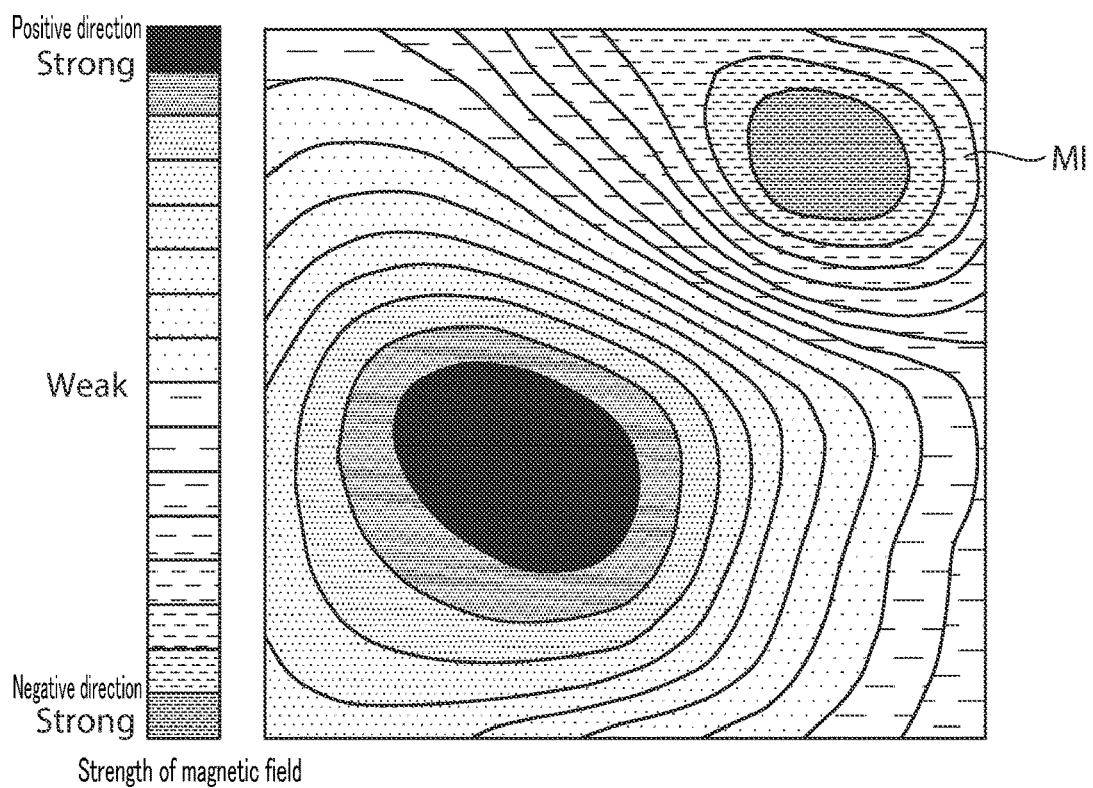
Figure 4:
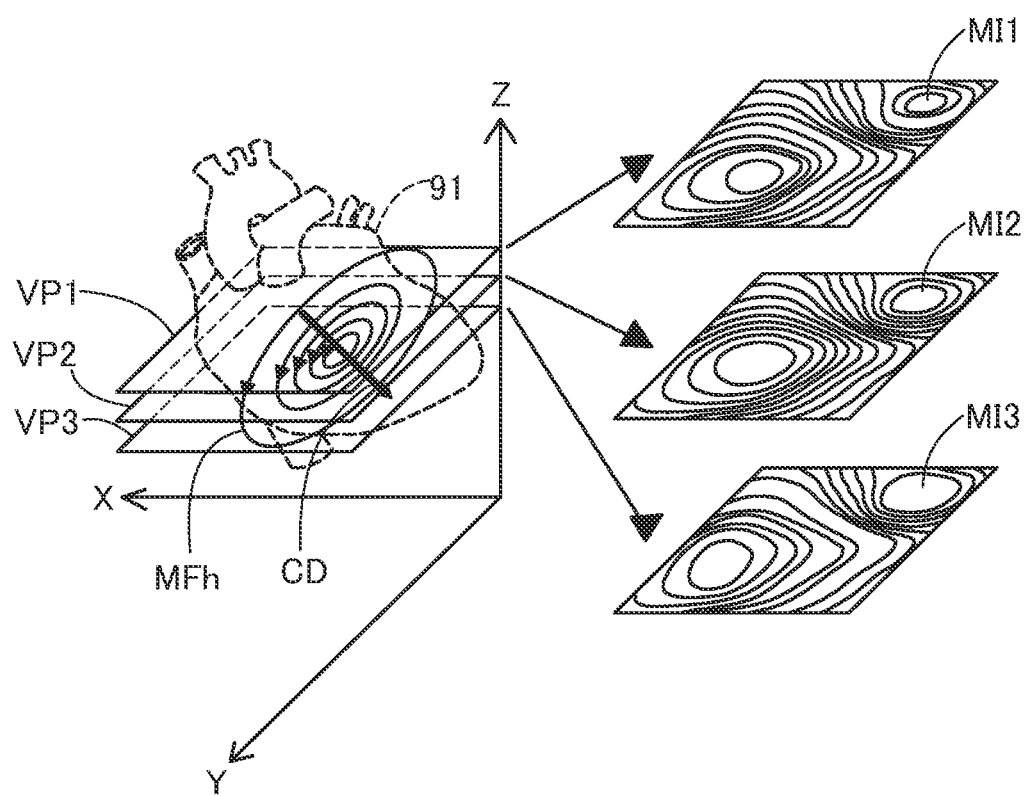
FIG. 4 is an explanatory diagram illustrating biomagnetic field distribution images in a plurality of virtual planes of a heart.

A method of generating the magnetic field distribution image (magnetocardiogram) MI by the magnetic distribution image generation portion 521 (FIG. 1) will be described with reference to FIGS. 2 to 4. FIG. 2 is an explanatory diagram schematically illustrating a method of detecting the biomagnetic field MFh by the magnetic sensor array 10. FIG. 3A is an explanatory diagram illustrating the strength (detection values Vd) of the biomagnetic field MFh detected by each of the magnetic sensors 11 of the magnetic sensor array 10. FIG. 3B is an explanatory diagram illustrating the biomagnetic field distribution image MI. FIG. 4 is an explanatory diagram illustrating the biomagnetic field distribution image MI in a plurality of virtual planes VP of the heart 91. Here, it is assumed that the main control portion 51 (FIG. 1) does not supply current to both the distal tip 22 and the marker 24, and no magnetic field is generated from the distal tip 22 and the marker 24. Therefore, the magnetic sensor array 10 outputs biomagnetic field information (the first magnetic field information) expressing the strength and orientation of the biomagnetic field MFh generated by the human body 90.

As illustrated in FIG. 2, in the heart 91, an electric signal CD is generated from a sinus node in order to contract an atrium and a ventricle. The magnetic sensor array 10 detects the strength and orientation of the biomagnetic field (cardiac magnetic field) MFh generated by the electric signal CD. In the magnetic sensor array 10, the magnetic sensors 11 are arranged in a matrix in a two-dimensional plane (XY plane), and thus, as illustrated in FIG. 3A, it is possible to detect the strength (the detection values Vd) of the biomagnetic field MFh at each position in the two-dimensional plane. FIG. 3A illustrates a time-series change of the strength of the biomagnetic field MFh at each position in the two-dimensional plane (XY plane). The orientation of the biomagnetic field MFh in the two-dimensional plane can be detected from a temporal change of the strength of the biomagnetic field MFh at each position in the two-dimensional plane. Further, the magnetic sensor 11 can detect a change in the strength of the biomagnetic field MFh in a direction (Z direction) normal to the two-dimensional plane. Here, each of the magnetic sensors 11 includes a plurality of (for example, two) elements arranged in a normal direction normal to the two-dimensional plane, and thus, it is possible to detect the strength of the biomagnetic field MFh at a position relatively close to the heart 91 and the strength of the biomagnetic field MFh at a position relatively far from the heart in the normal direction (Z direction). With this configuration, the magnetic sensor array 10 can detect the strength and orientation of the biomagnetic field MFh on any of the virtual planes (XY planes) VP into which the heart 91 is cut. The magnetic sensor array 10 outputs biomagnetic field information (the first magnetic field information) including the strength of these biomagnetic fields MFh detected by each of the magnetic sensors 11.

The magnetic distribution image generation portion 521 (FIG. 1) generates the biomagnetic field distribution image MI illustrated in FIG. 3B from the biomagnetic field information (the first magnetic field information) output from the magnetic sensor array 10. Here, as an example of the biomagnetic field distribution image MI, the strength of the biomagnetic field MFh (FIG. 3A) at each position in the two-dimensional plane (XY plane) is expressed by contour lines. A position where arrhythmia occurs can be identified, for example, by the shape of the contour lines of the biomagnetic field MFh. As illustrated in FIG. 4, the magnetic distribution image generation portion 521 can generate, from the biomagnetic field information (the first magnetic field information), the biomagnetic field distribution image MI on any of the virtual planes VP into which the heart 91 is cut. Here, biomagnetic field distribution images MI1, MI2, and MI3 corresponding to each of three virtual planes (a first virtual plane VP1, a second virtual plane VP2, and a third virtual plane VP3) are illustrated as an example.

Figure 5:
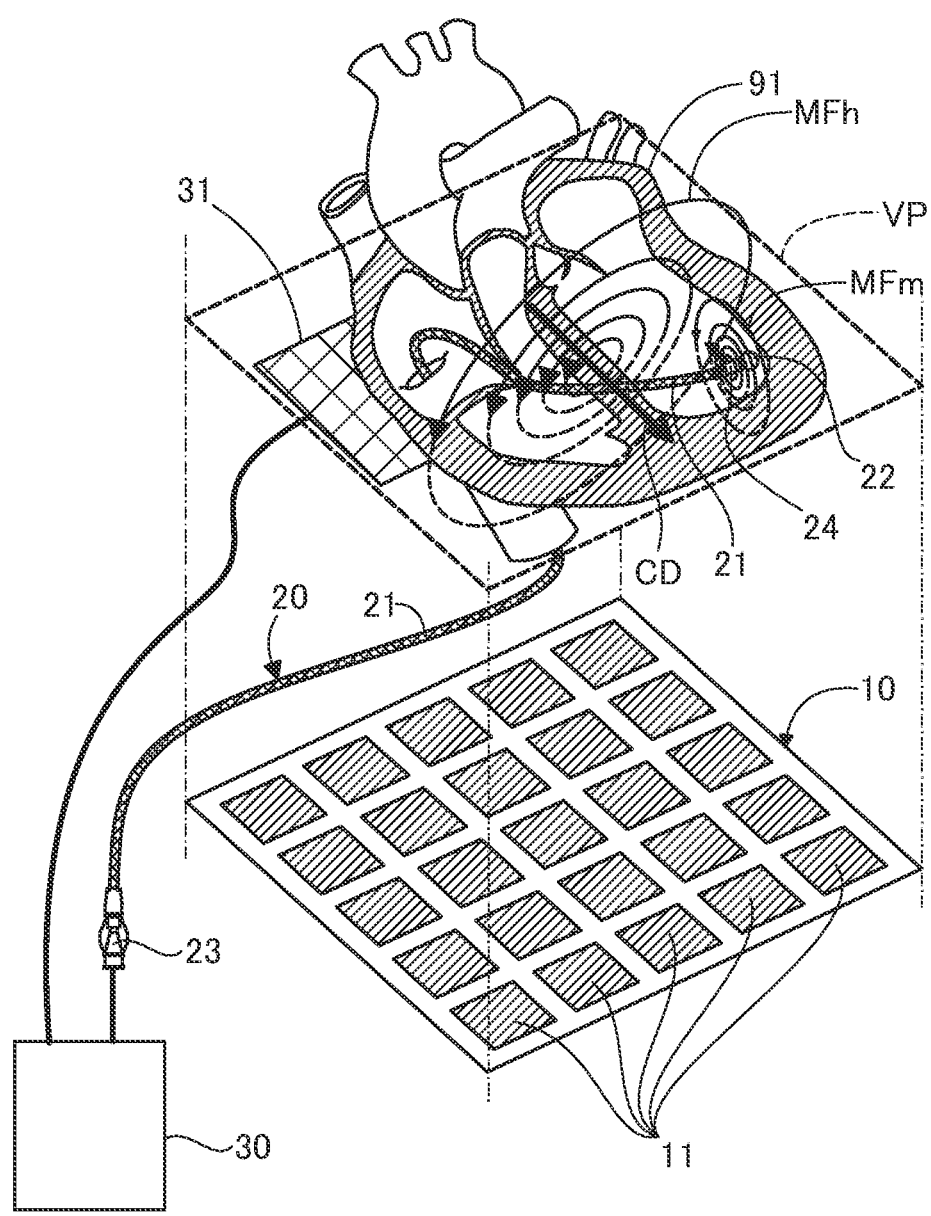
FIG. 5 is an explanatory diagram illustrating a method of detecting a combined magnetic field by the magnetic sensor array.
Figure 7:
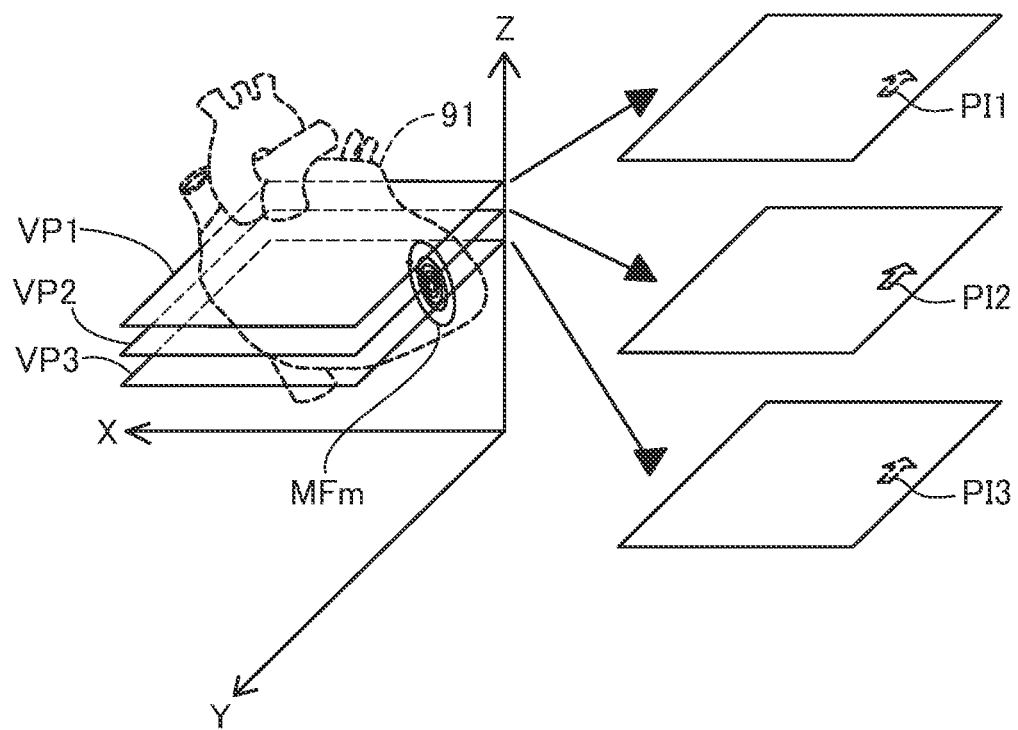
FIG. 7 is an explanatory diagram illustrating catheter position images on a plurality of virtual planes of a heart.

A method of generating the catheter position image PI by the position image generation portion 522 (FIG. 1) will be described with reference to FIGS. 5 to 7. FIG. 5 is an explanatory diagram schematically illustrating a method of detecting a combined biomagnetic/marker magnetic field by the magnetic sensor array 10. FIG. 6A is an explanatory diagram illustrating a combined magnetic field distribution image DMI. FIG. 6B is an explanatory diagram illustrating the catheter position image PI. FIG. 7 is an explanatory diagram illustrating the catheter position image PI in a plurality of the virtual planes VP of the heart 91. Here, it is assumed that the main control portion 51 (FIG. 1) supplies a detection current to the marker 24, and the marker magnetic field MFm is generated by the marker 24. The magnetic sensor array 10 outputs the second magnetic field information expressing the strength and orientation of the combined biomagnetic/marker magnetic field in which both the biomagnetic field MFh generated by the human body 90 and the marker magnetic field MFm generated by the marker 24 are combined.

The detection current flows in the marker 24, and thus, the marker magnetic field MFm is generated by the marker 24, as illustrated in FIG. 5. Further, the biomagnetic field (cardiac magnetic field) MFh is generated by the electric signal CD from the heart 91. The magnetic sensor array 10 detects the strength and orientation of the combined biomagnetic/marker magnetic field in which the marker magnetic field MFm and the biomagnetic field MFh are combined. With the above-described configuration, the magnetic sensor array 10 can detect the strength and orientation of the combined biomagnetic/marker magnetic field at each position in the two-dimensional plane. Further, the magnetic sensor array 10 can detect the strength and orientation of the combined biomagnetic/marker magnetic field in any one of the virtual planes (XY planes) VP into which the heart 91 is cut. The magnetic sensor array 10 outputs the second magnetic field information including the strength of these combined biomagnetic/marker magnetic fields detected by each of the magnetic sensors 11.

The position image generation portion 522 (FIG. 1) generates the combined magnetic field distribution image DMI illustrated in FIG. 6A from the second magnetic field information output from the magnetic sensor array 10. Here, as an example of the combined magnetic field distribution image DMI, the strength of the combined biomagnetic/marker magnetic field at each position in the two-dimensional plane (XY plane) is expressed by contour lines. The contour lines of the combined magnetic field distribution image DMI include a part affected by the biomagnetic field MFh and a part affected by the marker magnetic field MFm. The position image generation portion 522 identifies the part affected by the marker magnetic field MFm by comparing the biomagnetic field distribution image MI (FIG. 3B) generated by the magnetic distribution image generation portion 521 and the combined magnetic field distribution image DMI. That is, the biomagnetic field distribution image MI of FIG. 3B is substantially unaffected by the marker magnetic field MFm and is formed by the biomagnetic field (cardiac magnetic field) MFh. On the other hand, the combined magnetic field distribution image DMI is formed by the biomagnetic field (cardiac magnetic field) MFh and the marker magnetic field MFm. Thus, from the difference between these two images, it is possible to identify a part of the combined magnetic field distribution image DMI affected by the marker magnetic field MFm. Therefore, it is possible to identify the position of the marker 24 in the combined magnetic field distribution image DMI. Further, the orientation of the marker 24 at the identified position can be determined from the shape of the contour line of the part affected by the marker magnetic field MFm. Moreover, by comparing the shape of the contour lines of parts affected by the marker magnetic field MFm in each of the combined magnetic field distribution images DMI of a plurality of virtual planes having different positions in the Z direction, it is possible to identify not only the position and the orientation of the marker 24 in the XY plane, but also a position, an orientation, and an inclination (rotation) of the marker 24 in three dimensions including an X direction.

The position image generation portion 522 (FIG. 1) identifies the position, the orientation, and the inclination (rotation) of the marker 24 in the combined magnetic field distribution image DMI, and then generates the catheter position image PI of FIG. 6B. The catheter position image PI is an image in which a contour line is deleted or made invisible in the combined magnetic field distribution image DMI, and an icon indicating the position of the distal end portion of the catheter 20 is arranged at the identified position of the marker 24. Here, an arrow shape is illustrated as an icon. The catheter position image PI represents the position and orientation of the distal end portion of the catheter 20 according to the position and orientation of the arrow. Here, as will be described later, the catheter position image PI is expressed by a stereoscopic image of an arrow, and the inclination (rotation) of the distal end portion of the catheter 20 can be expressed by changing the shape of the arrow to an inclined shape.

The position image generation portion 522 (FIG. 1) can generate, from the second magnetic field information, the combined magnetic field distribution image DMI in any of the virtual planes VP into which the heart 91 is cut. Further, as illustrated in FIG. 7, the catheter position image PI in any of the virtual planes VP can be generated by comparing the biomagnetic field distribution images MI (FIG. 3B) in the corresponding virtual planes VP. Here, catheter position images PI1, PI2, and PI3 corresponding to each of the three virtual planes (the first virtual plane VP1, the second virtual plane VP2, and the third virtual plane VP3) are illustrated as an example. The position image generation portion 522 (FIG. 1) can also identify the position of the marker 24 in the Z direction by comparing the combined magnetic field distribution image DMI and the corresponding biomagnetic field distribution image MI in any of the virtual planes VP. Thus, here, the position image generation portion 522 (FIG. 1) expresses the position of the marker 24 in the Z direction by a contour of the catheter position image PI. Specifically, in the virtual plane (XY plane) VP that coincides with the position of the marker 24 in the Z direction, the contour of the catheter position image PI is illustrated by a solid line, and in the virtual plane (XY plane) VP that does not coincide with the position of the marker 24 in the Z direction, the contour of the catheter position image PI is illustrated by a broken line. Here, the contour of the catheter position image PI2 is illustrated by a solid line, and the contours of the catheter position images PI1 and PI3 are illustrated by broken lines. From this, it can be understood that the position of the distal end of the catheter 20 in the Z direction coincides with the second virtual plane VP2. With this configuration, the position of the distal end of the catheter in the Z direction can be easily identified.

A method of generating the combined image CI by the combined image generation portion 523 (FIG. 1) will be described with reference to FIG. 8. FIG. 8 is a schematic diagram for describing the method of generating the combined image CI. The combined image generation portion 523 (FIG. 1) superimposes the biomagnetic field distribution image MI generated by the magnetic distribution image generation portion 521 and the catheter position image PI generated by the position image generation portion 522 (FIG. 1) to generate the combined image CI in which the catheter position image PI is displayed on the biomagnetic field distribution image MI. The combined image CI illustrates a position of the distal end portion of the catheter 20 relative to the biomagnetic field distribution. The combined image generation portion 523 generates the combined image CI by superimposing the biomagnetic field distribution image MI and the catheter position image PI for each of the virtual planes VP. Here, an example is illustrated in which the combined image generation portion 523 generates a combined image CI1 by superimposing the biomagnetic field distribution image MI1 and the catheter position image PI1 corresponding to the first virtual plane VP1, generates a combined image CI2 by superimposing the biomagnetic field distribution image MI2 and the catheter position image PI2 corresponding to the second virtual plane VP2, and generates a combined image CI3 by superimposing the biomagnetic field distribution image MI3 and the catheter position image PI3 corresponding to the third virtual plane VP3.

The generated combined image CI is displayed on the display screen 61 by the main control portion 51. The image information processing portion 52 continuously generates the combined images CI at predetermined intervals, and the display screen 61 displays the combined image CI in real time, that is, the real-time biomagnetic field distribution and the position of the distal end portion of the catheter 20 relative to the real-time biomagnetic field distribution. The main control portion 51 causes the display screen 61 to display the combined image CI corresponding to any of the virtual planes VP, in accordance with an operation by the operating portion 70. For example, if the main control portion 51 receives an operation for the operating portion 70 to display a virtual plane on a +Z direction side, while the main control portion 51 displays the combined image CI2 corresponding to the second virtual plane VP2, the main control portion 51 displays the combined image CI1 corresponding to the first virtual plane VP1. Further, if the main control portion 51 receives an operation for the operating portion 70 to display a virtual plane on a −Z direction side, while the main control portion 51 displays the combined image CI2 corresponding to the second virtual plane VP2, the main control portion 51 displays the combined image CI3 corresponding to the third virtual plane VP3.

Figure 9A:
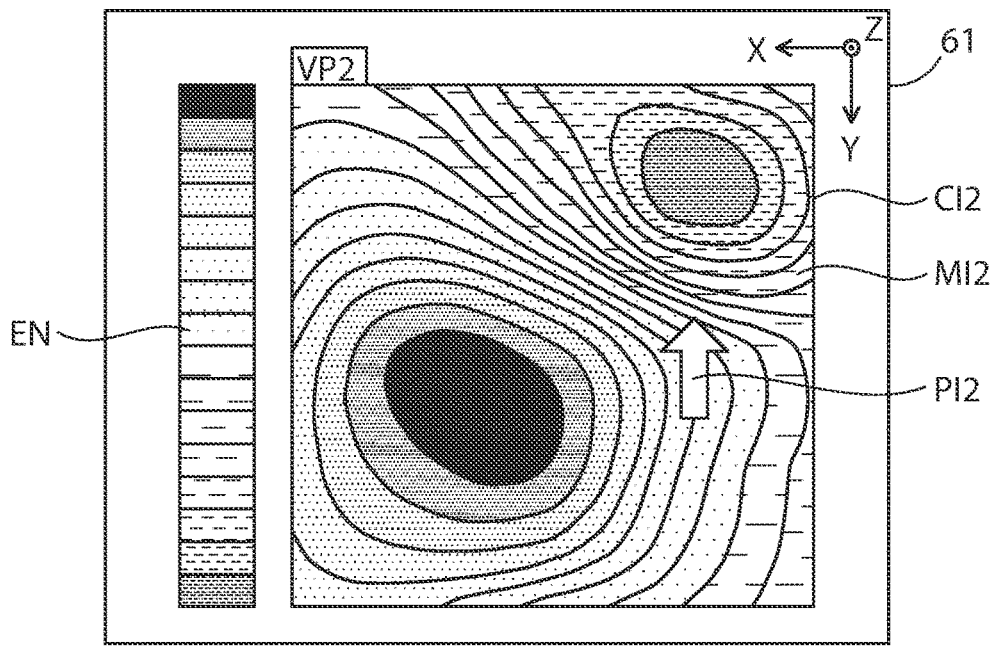
FIGS. 9A and 9B are first explanatory diagrams illustrating display examples of a combined image corresponding to a second virtual plane.
Figure 9B:
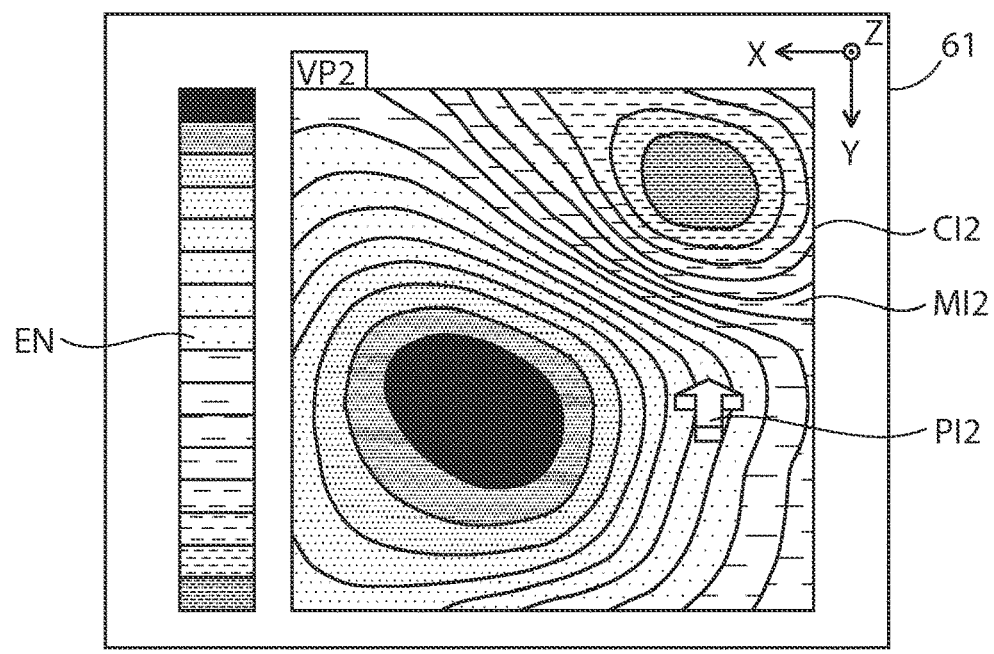
Figure 10A:
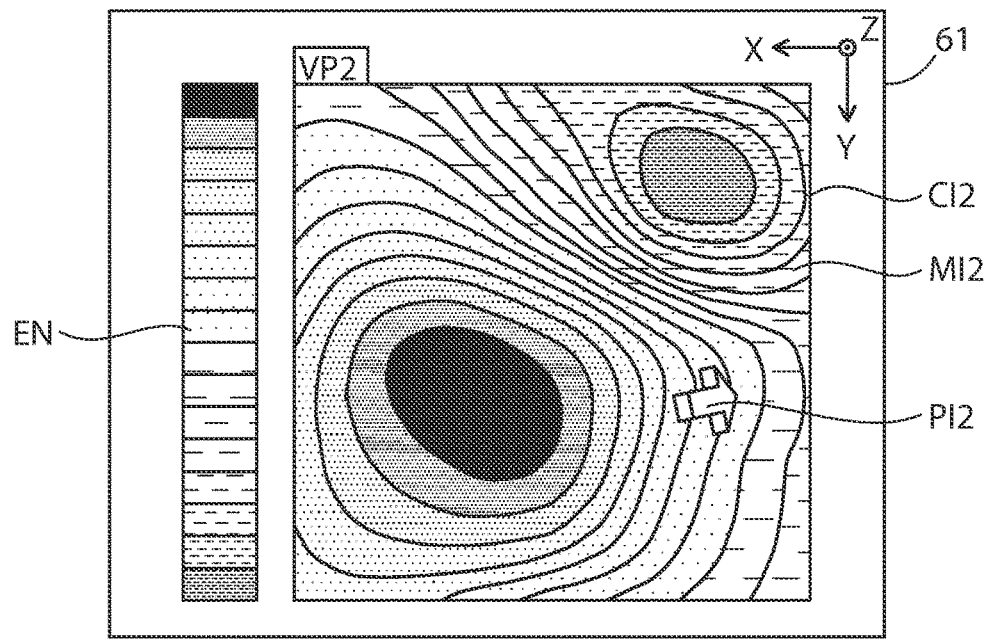
FIGS. 10A and 10B are second explanatory diagrams illustrating display examples of a combined image corresponding to the second virtual plane.
Figure 10B:
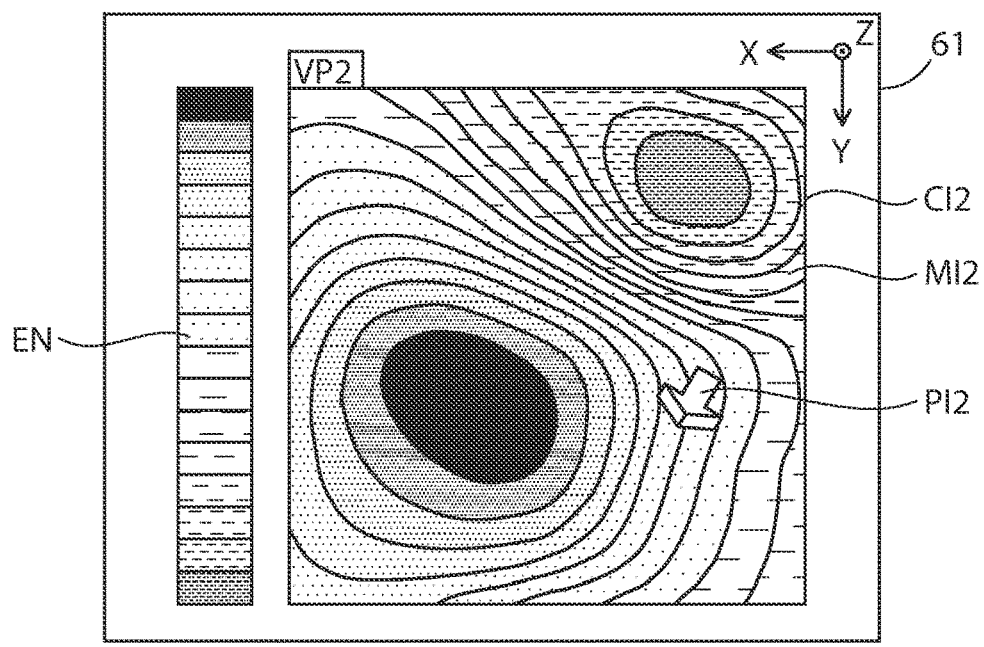
Figure 11A:
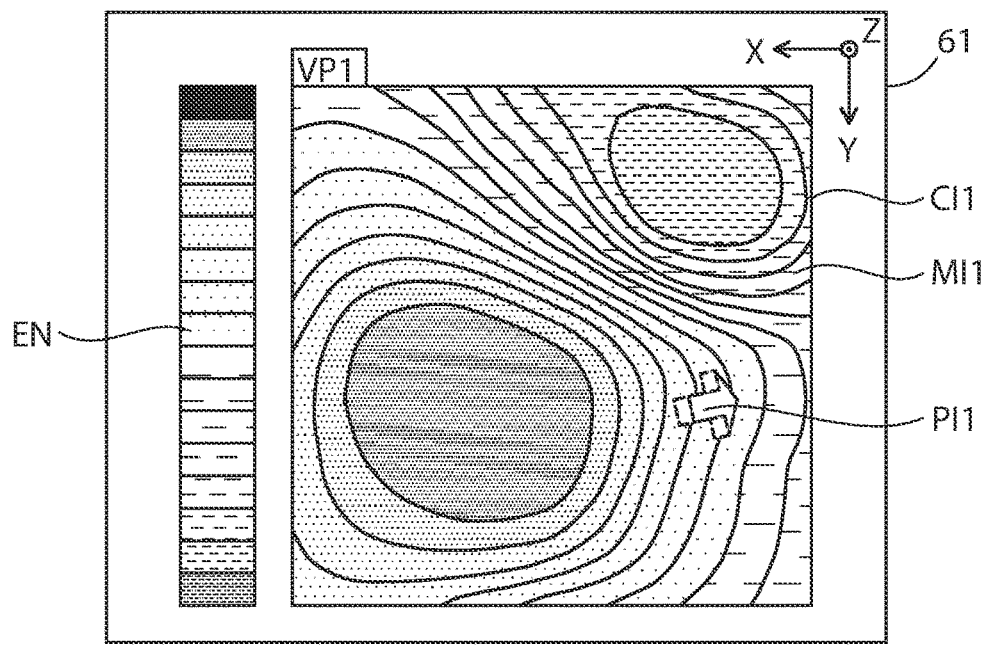
FIGS. 11A and 11B are explanatory diagrams illustrating display examples of a combined image corresponding to first and third virtual planes.
Figure 11B:
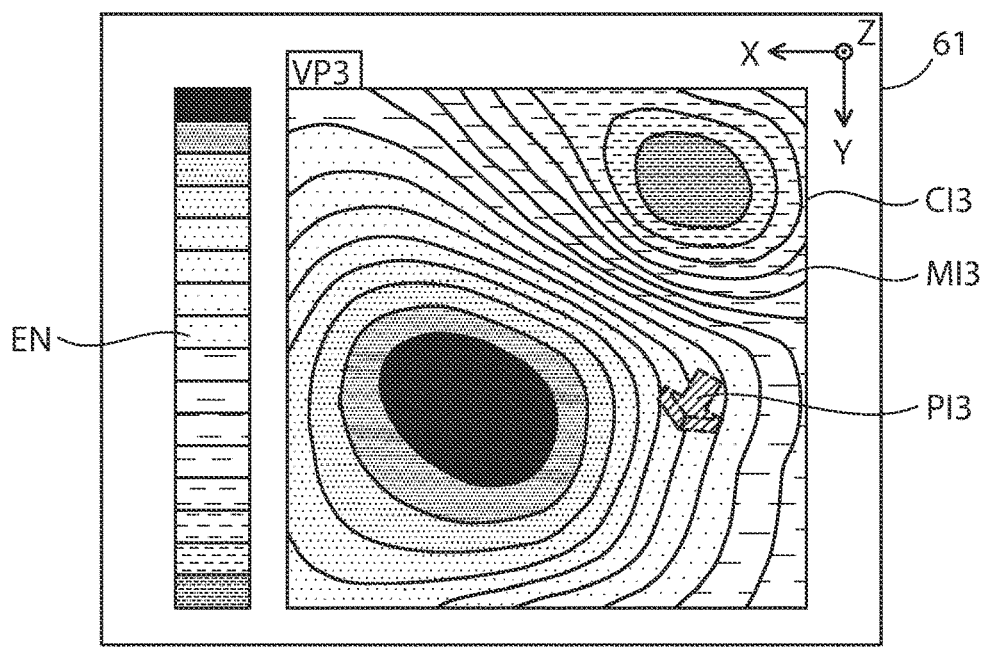

A display example of the combined image CI displayed on the display screen 61 will be described with reference to FIGS. 9A and 9B to 11A and 11B. FIG. 9A is an explanatory diagram illustrating a first display example of the combined image CI2 corresponding to the second virtual plane VP2. FIG. 9B is an explanatory diagram illustrating a second display example of the combined image CI2. FIG. 10A is an explanatory diagram illustrating a third display example of the combined image CI2. FIG. 10B is an explanatory diagram illustrating a fourth display example of the combined image CI2. FIGS. 9A, 9B, 10A, and 10B are identical, except that the arrow shapes of the catheter position image PI2 are different from each other. FIG. 11A is an explanatory diagram illustrating a display example of the combined image CI1 corresponding to the first virtual plane VP1. FIG. 11B is an explanatory diagram illustrating a display example of the combined image CI3 corresponding to the third virtual plane VP3. A display content is switched from the combined images CI2 of FIGS. 9A, 9B, 10A, and 10B to the combined image CI1 of FIG. 11A, and from the combined images CI2 of FIGS. 9A, 9B, 10A, and 10B to the combined image CI3 of FIG. 11B, in accordance with an operation of the operating portion 70. That is, the main control portion 51 causes the display screen 61 to display the combined image CI corresponding to the virtual plane VP at any position in the Z direction, in accordance with the operation of the operating portion 70.

As illustrated in FIG. 9A, the combined image CI2 corresponding to the second virtual plane VP2 and a legend EN thereof are displayed on the display screen 61. The combined image CI2 includes the biomagnetic field distribution image MI2 and the catheter position image PI2. A position of the catheter position image PI2 relative to the biomagnetic field distribution image MI2 indicates the position of the distal end portion of the catheter 20 relative to the biomagnetic field distribution. An orientation of the arrow in the catheter position image PI2 indicates the orientation of the distal end portion of the catheter 20 with respect to the biomagnetic field distribution. In FIG. 9A, the catheter position image PI2 has the shape of an arrow pointing straight upward in parallel with the plane (XY plane) of the display screen 61. The contour of the arrow is illustrated by a solid line. From this, it can be understood that the distal end of the catheter 20 is located on the second virtual plane VP2 of the heart 91, is parallel to the second virtual plane VP2, and faces a −Y direction.

In FIG. 9B, the catheter position image PI2 has the shape of an arrow that is not parallel to the plane (XY plane) of the display screen 61, and points upward from a front side toward a back side of the display screen 61. The contour of the arrow is illustrated by a solid line. From this, it can be understood that the distal end of the catheter 20 is positioned on the second virtual plane VP2 of the heart 91 and faces the −Y direction and the −Z direction. In FIG. 10A, the catheter position image PI2 has the shape of an arrow that is not parallel to the plane (XY plane) of the display screen 61, points right upward from the front side toward the back side of the display screen 61, and is inclined to the right (rotated to the right). The contour of the arrow is illustrated by a solid line. From this, it can be understood that the distal end of the catheter 20 is positioned on the second virtual plane VP2 of the heart 91, faces a −X direction, the −Y direction, and the −Z direction, and is inclined to the right (rotated to the right). In FIG. 10B, the catheter position image PI2 has the shape of an arrow that is not parallel to the plane (XY plane) of the display screen 61, points left downward from the back side toward the front side of the display screen 61, and is inclined to the right (rotated to the right). The contour of the arrow is illustrated by a solid line. From this, it can be understood that the distal end of the catheter 20 is positioned on the second virtual plane VP2 of the heart 91, faces a +X direction, a +Y direction, and the +Z direction, and is inclined to the right (rotated to the right).

The combined image CI1 corresponding to the first virtual plane VP1 and the legend EN thereof are displayed on the display screen 61 of FIG. 11A. The combined image CI1 includes the biomagnetic field distribution image MI1 and the catheter position image PI1. The catheter position image PI1 of FIG. 11A is different from the catheter position image PI2 of FIG. 10A in that the contour of the arrow is illustrated by a broken line. This indicates that the distal end of the catheter 20 is not in the displayed first virtual plane VP1. In the catheter position image PI1 of FIG. 11A, a part within the contour of the broken line is displayed in white. This indicates that the position of the distal end of the catheter 20 in the Z direction is located more to the −Z direction than the displayed first virtual plane VP1.

The combined image CI3 corresponding to the third virtual plane VP3 and the legend EN thereof are displayed on the display screen 61 of FIG. 11B. The combined image CI3 includes the biomagnetic field distribution image MI3 and the catheter position image PI3. The catheter position image PI3 of FIG. 11B is different from the catheter position image PI2 of FIG. 10B in that the contour of the arrow is illustrated by a broken line, and the color of a part within the contour of the broken line is different. The fact that the contour of the arrow is a broken line indicates that the distal end of the catheter 20 is not on the displayed third virtual plane VP3. The fact that the color of the part within the contour of the broken line is different, indicates that the position of the distal end of the catheter 20 in the Z direction is located more to the +Z direction than the displayed third virtual plane VP3.

Examples of Effects of Present Embodiment

According to the treatment system 1 of the present embodiment described above, the combined image CI including the biomagnetic field distribution image MI expressing the strength of the biomagnetic field and the catheter position image PI expressing the position of the catheter 20 is displayed on the display screen 61. Thus, an operator of the catheter 20 can perform a treatment while confirming the displayed combined image CI. Therefore, it is possible to improve the convenience during treatment.

Further, according to the treatment system 1 of the present embodiment, in the biomagnetic field distribution image MI, the strength of the biomagnetic field MFh (FIG. 3A) at each position of a two-dimensional plane (XY plane) is further expressed by contour lines and the catheter position image PI2 is displayed on the contour lines. Thus, the operator of the catheter 20 can confirm the position of the distal end portion of the catheter 20 relative to the biomagnetic field distribution. Therefore, it is possible to further improve the convenience.

Further, according to the treatment system 1 of the present embodiment, the display screen 61 displays the biomagnetic field distribution in real time and the position of the distal end portion of the catheter 20 relative to the biomagnetic field distribution. Therefore, it is possible to provide the operator of the catheter 20 in real time with the position of the ablation catheter with respect to a location where arrhythmia occurs. Further, by confirming the biomagnetic field distribution after ablation, it is possible to confirm whether or not a biomagnetic field distribution indicating arrhythmia disappears, without removing the ablation catheter.

Second Embodiment

Figure 12:
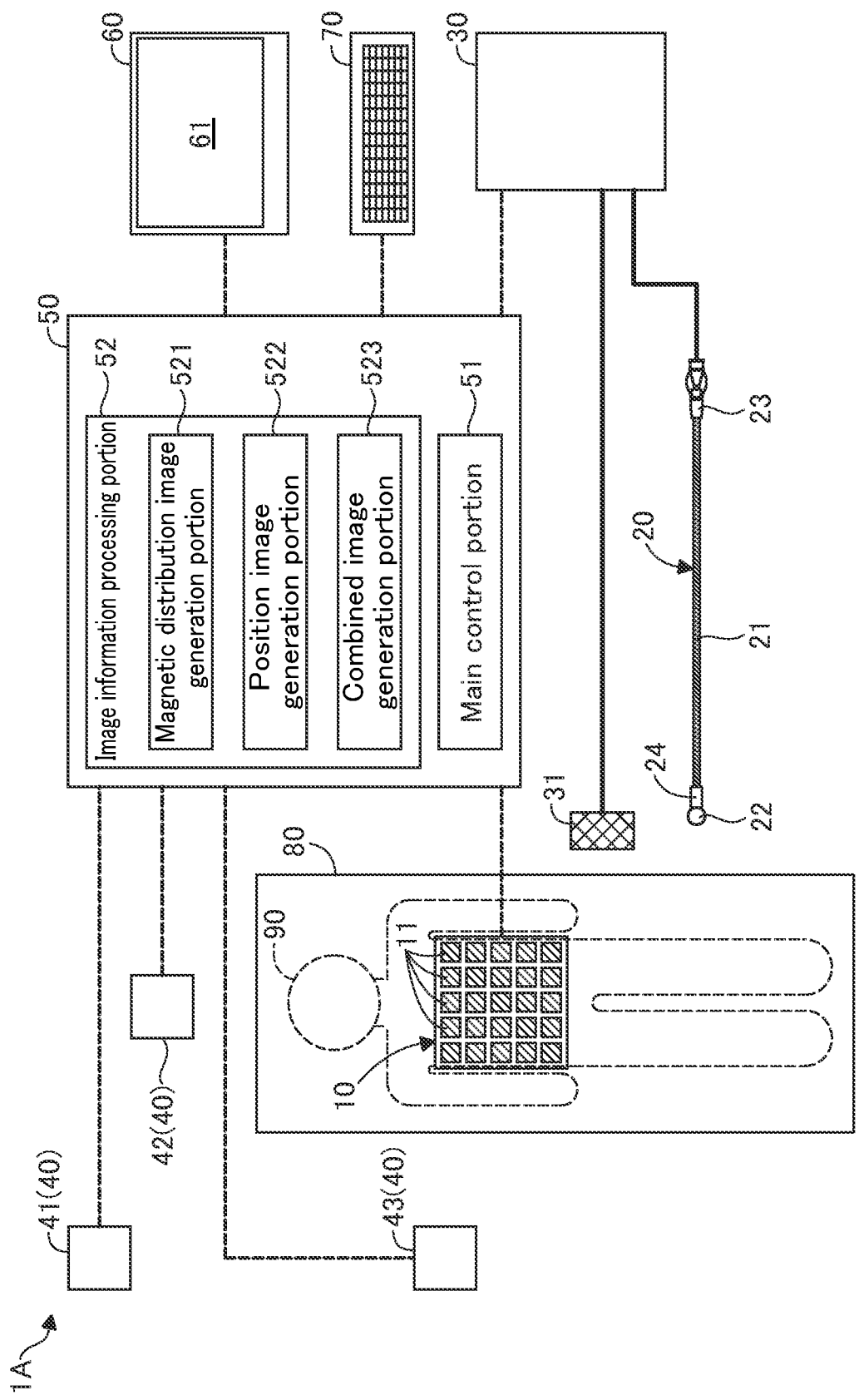
FIG. 12 is an explanatory diagram illustrating a simplified configuration of a treatment system of a second embodiment.

FIG. 12 is an explanatory diagram illustrating a simplified configuration of a treatment system 1A of a second embodiment. The treatment system 1A of the second embodiment is different from the treatment system 1 of the first embodiment (FIG. 1) in that the treatment system 1A further includes a position detection portion 40. Other parts of the configuration are similar to those of the treatment system 1 of the first embodiment, and thus, description thereof will be omitted. The position detection portion 40 includes three sensors 41, 42, and 43, and detects a three-dimensional position of the catheter 20. The three sensors 41, 42, and 43 are arranged at different positions in a three-dimensional space, and detect the strength and orientation of the marker magnetic field MFm generated by the marker 24. Here, the main control portion 51 controls a current for position detection supplied to the marker 24, so that the marker magnetic field MFm is very large with respect to the biomagnetic field (cardiac magnetic field) MFh. The marker magnetic field MFm is much larger than the biomagnetic field MFh, and thus, an influence of the biomagnetic field MFh included in a magnetic field detected by the position detection portion 40 is substantially negligible.

When supplying the detection current to the marker 24, the main control portion 51 acquires, from the position detection portion 40, information about the strength and orientation of the magnetic field detected by the position detection portion 40 (hereinafter, also referred to as "third magnetic field information"). The third magnetic field information is magnetic field information that represents the strength and orientation of the marker magnetic field MFm generated by the marker 24 and in which the biomagnetic field MFh generated by the human body 90 is substantially not included. The third magnetic field information includes information about the marker magnetic field MFm, and thus, it can be said that the third magnetic field information includes position information of the catheter 20.

Figure 13:
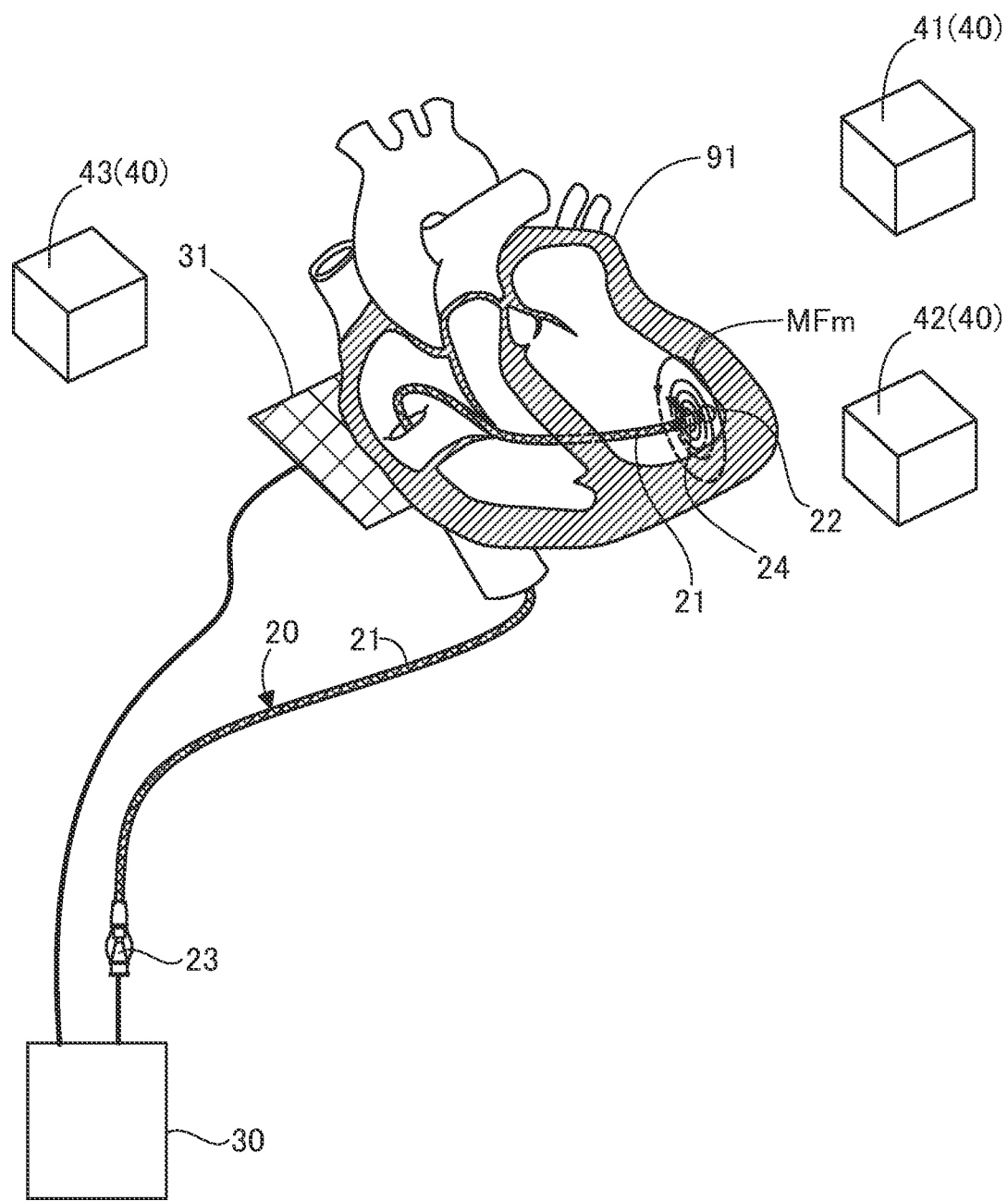
FIG. 13 is an explanatory diagram illustrating a method of detecting a position of a catheter by a position detection portion.
Figure 14A:
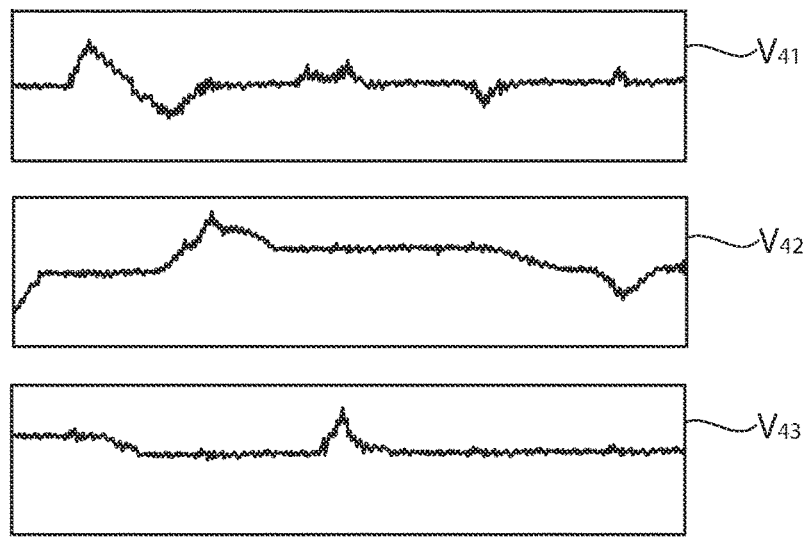
FIGS. 14A and 14B are explanatory diagrams illustrating a strength of a marker magnetic field detected by each sensor.
Figure 14B:
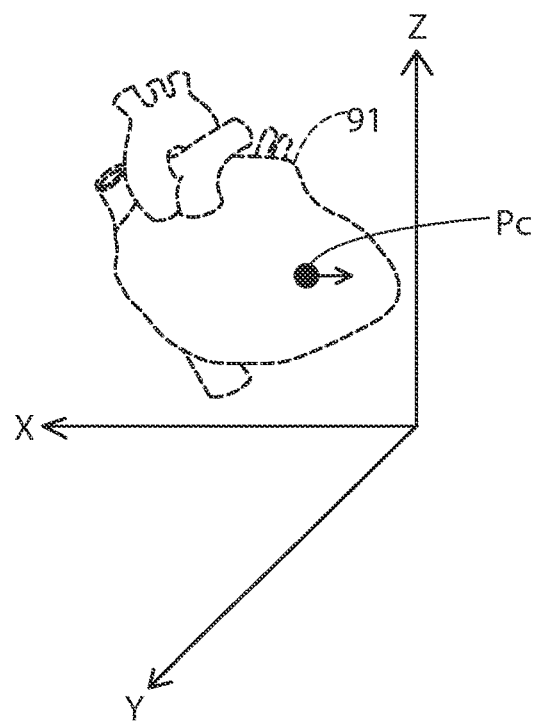

A method of detecting the position of the catheter 20 by the position detection portion 40 will be described with reference to FIGS. 13 and 14. FIG. 13 is an explanatory diagram schematically illustrating the method of detecting the position of the catheter 20 by the position detection portion 40. In FIG. 13, the biomagnetic field MFh is not illustrated. FIG. 14A is an explanatory diagram illustrating the strength of the marker magnetic field MFm detected by each of the sensors 41, 42, and 43. FIG. 14B is an explanatory diagram schematically illustrating the position of the distal end portion of the catheter 20.

As illustrated in FIG. 13, the position detection portion 40 detects the strength of the marker magnetic field MFm from different positions by the three sensors 41, 42, and 43. As described above, the biomagnetic field MFh generated by the heart 91 is much weaker than the marker magnetic field MFm, and thus, the influence of the biomagnetic field MFh is substantially negligible. As illustrated in FIG. 14A, the position detection portion 40 outputs the third magnetic field information including strengths $V_{41}$, $V_{42}$, and $V_{43}$ of the marker magnetic field MFm detected by each of the sensors 41, 42, and 43. The position image generation portion 522 generates the catheter position image PI (FIG. 6B) from the third magnetic field information. The position image generation portion 522 identifies a position Pc and an orientation (arrow) of the catheter 20 in a three-dimensional space, as illustrated in FIG. 14B, from a temporal change of the marker magnetic field MFm detected by each of the sensors 41, 42, and 43. Thus, the position image generation portion 522 can generate, from the third magnetic field information, the catheter position image PI in any of the virtual planes VP into which the heart 91 is cut.

Similarly to the first embodiment, the combined image generation portion 523 superimposes the biomagnetic field distribution image MI generated by the magnetic distribution image generation portion 521 and the catheter position image PI generated by the position image generation portion 522 to generate the combined image CI in which the catheter position image PI is displayed on the biomagnetic field distribution image MI. The generated combined image CI is displayed on the display screen 61 by the main control portion 51. A display example of the combined image CI displayed on the display screen 61 is similar to that of the first embodiment, and thus, description thereof will be omitted.

According to the treatment system 1A of the present embodiment described above, the sensor that identifies the position of the catheter 20 is not limited to the magnetic sensor array 10, and any other sensor can be adopted. With the treatment system 1A of the present embodiment in which the position of the catheter 20 is identified by a sensor other than the magnetic sensor array 10, it is also possible to generate the combined image CI including the biomagnetic field distribution image MI expressing the strength of the biomagnetic field and the catheter position image PI expressing the position of the catheter 20, and thus, an operator can perform a treatment while confirming the combined image CI. Therefore, it is possible to improve the convenience during treatment.

Third Embodiment

Figure 15A:
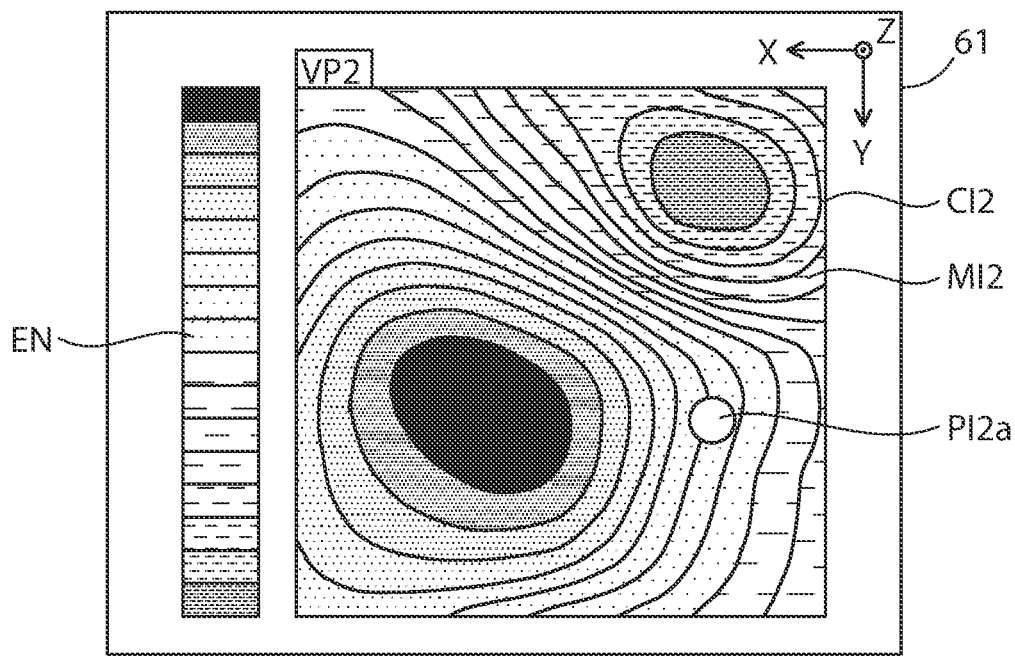
FIGS. 15A and 15B are explanatory diagrams illustrating display examples of a combined image in a third embodiment.
Figure 15B:
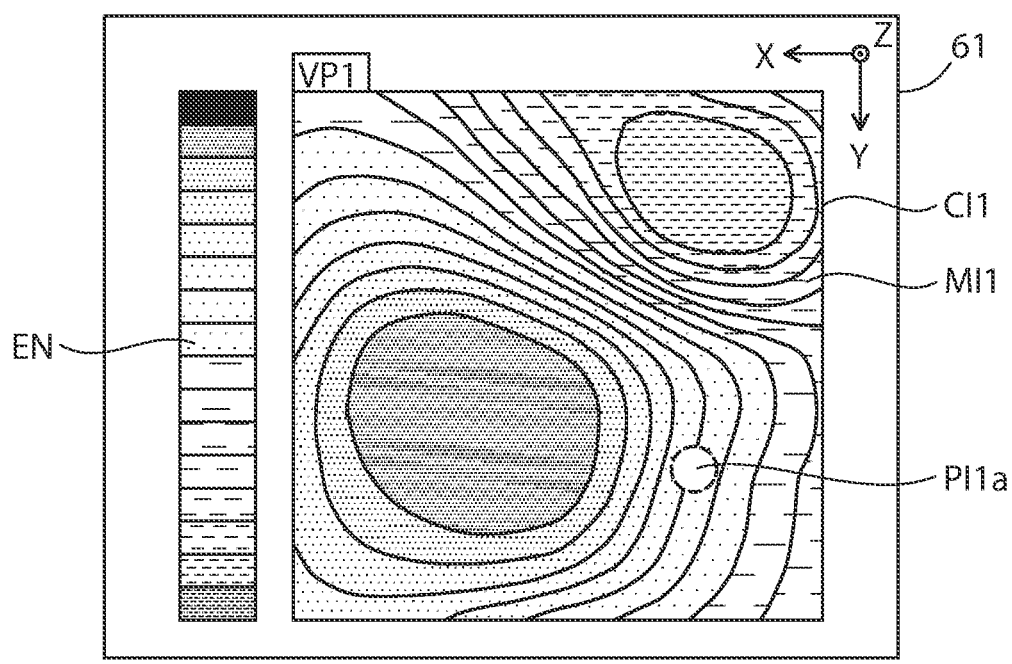

FIGS. 15A and 15B are explanatory diagrams illustrating display examples of the combined image CI in a third embodiment. FIG. 15A is an explanatory diagram illustrating a display example of the combined image CI2 corresponding to the second virtual plane VP2. FIG. 15B is an explanatory diagram illustrating a display example of the combined image CI1 corresponding to the first virtual plane VP1. The display examples of the third embodiment are different from the display examples of the first embodiment in that the shape of the catheter position image PI included in the combined image CI is different. Other parts of the configuration are similar to those of the first embodiment, and thus, description thereof will be omitted.

As illustrated in FIG. 15A, the combined image CI2 corresponding to the second virtual plane VP2 and the legend EN thereof are displayed on the display screen 61. The combined image CI2 includes the biomagnetic field distribution image MI2 and a catheter position image PI2a. The catheter position image PI2a of FIG. 15A has the shape of a white circle, and a position of the catheter position image PI2a relative to the biomagnetic field distribution image MI2 indicates the position of the distal end portion of the catheter 20 relative to the biomagnetic field distribution. Unlike the first embodiment, the catheter position image PI2a is a non-directional image and does not include information about the orientation of the distal end portion of the catheter 20.

The combined image CI1 corresponding to the first virtual plane VP1 and the legend EN thereof are displayed on the display screen 61 of FIG. 15B. The combined image CI1 includes the biomagnetic field distribution image MI1 and a catheter position image PI1a. The catheter position image PI1a of FIG. 15B is different from the catheter position image PI2a of FIG. 15A in that the contour of the circle is illustrated by a broken line. This indicates that the distal end of the catheter 20 is not in the displayed first virtual plane VP1. In the catheter position image PI1a of FIG. 15B, a part within the contour of the broken line is displayed in white. This indicates that, in the catheter position image PI1a, the position of the distal end portion of the catheter 20 in the Z direction is located more to the −Z direction than the currently displayed first virtual plane VP1. If the part within the contour of the broken line is displayed in a different color in the catheter position image PI1a, this indicates that the position of the distal end portion of the catheter 20 in the Z direction is located more to the +Z direction than the illustrated virtual plane VP.

According to the display examples of the combined image CI of the present embodiment described above, the shape of the catheter position image PI1a is not limited to the arrow, and any shape can be adopted. Even in this case, the combined image CI includes the biomagnetic field distribution image MI expressing the strength of the biomagnetic field and the catheter position image PI expressing the position of the catheter 20, and thus, an operator of the catheter 20 can perform a treatment while confirming the combined image CI. Therefore, it is possible to improve the convenience during treatment.

Fourth Embodiment

Figure 16:
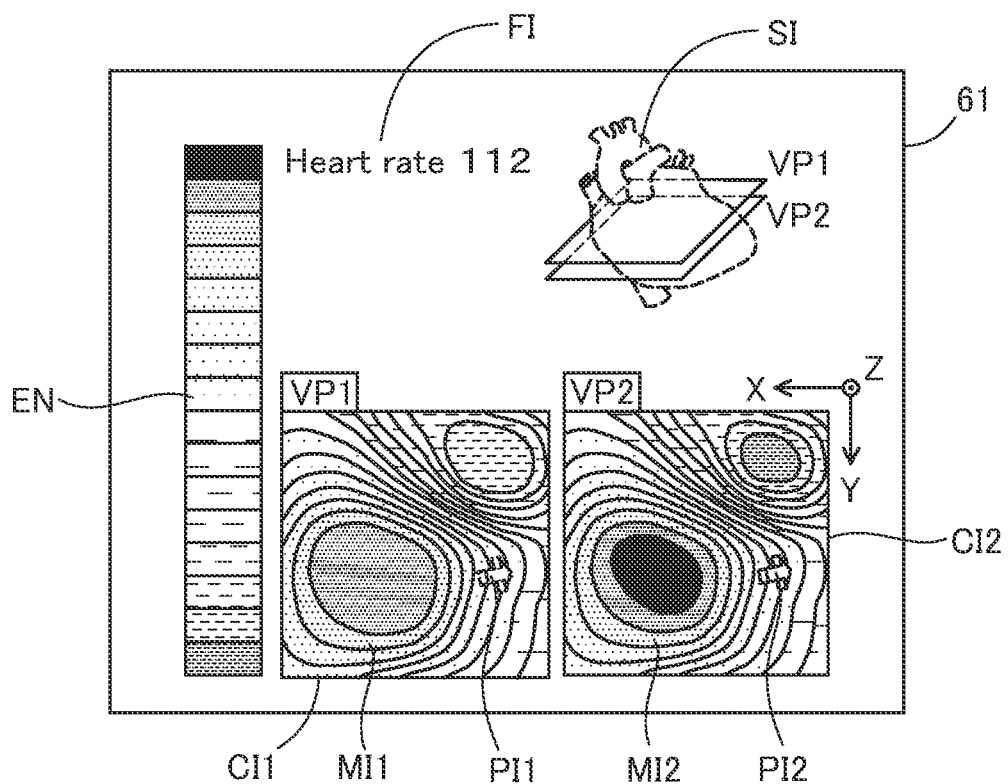
FIG. 16 is an explanatory diagram illustrating a display example of a combined image in a fourth embodiment.

FIG. 16 is an explanatory diagram illustrating a display example of the combined image CI in a fourth embodiment. The display example of the fourth embodiment is different from the display examples of the first embodiment regarding the number of the combined images CI displayed on the display screen 61. Further, an image not displayed in the first embodiment is additionally displayed. Other parts of the configuration are similar to those of the first embodiment, and thus, description thereof will be omitted.

As illustrated in FIG. 16, the combined image CI1 corresponding to the first virtual plane VP1, the combined image CI2 corresponding to the second virtual plane VP2, a heart model image SI, a heart rate display image FI, and the legend EN are displayed on the display screen 61. The combined image CI1 includes the biomagnetic field distribution image MI1 and the catheter position image PI1. The combined image CI2 includes the biomagnetic field distribution image MI2 and the catheter position image PI2. In the heart model image SI, the positions of the virtual planes VP corresponding to the two displayed combined images CI are displayed. The heart rate display image FI contains a number indicating a heart rate of the heart 91.

The two combined images CI displayed on the display screen 61 can be switched by an operation of the operating portion 70. The main control portion 51 causes the display screen 61 to display the two combined images CI corresponding to each of the virtual planes VP at any two positions in the Z direction, in accordance with the operation of the operating portion 70. If the displayed combined image CI is switched, the position of the virtual plane VP displayed on the heart model image SI is also switched.

According to the display example of the combined image CI of the present embodiment described above, the number of the catheter position images PI displayed on the display screen 61 is not limited to one, and can be any number. Even in this case, if a plurality of the combined images CI are displayed, an operator of the catheter 20 can perform treatment while simultaneously confirming the plurality of combined images CI. Therefore, it is possible to further improve the convenience during treatment.

Fifth Embodiment

Figure 17:
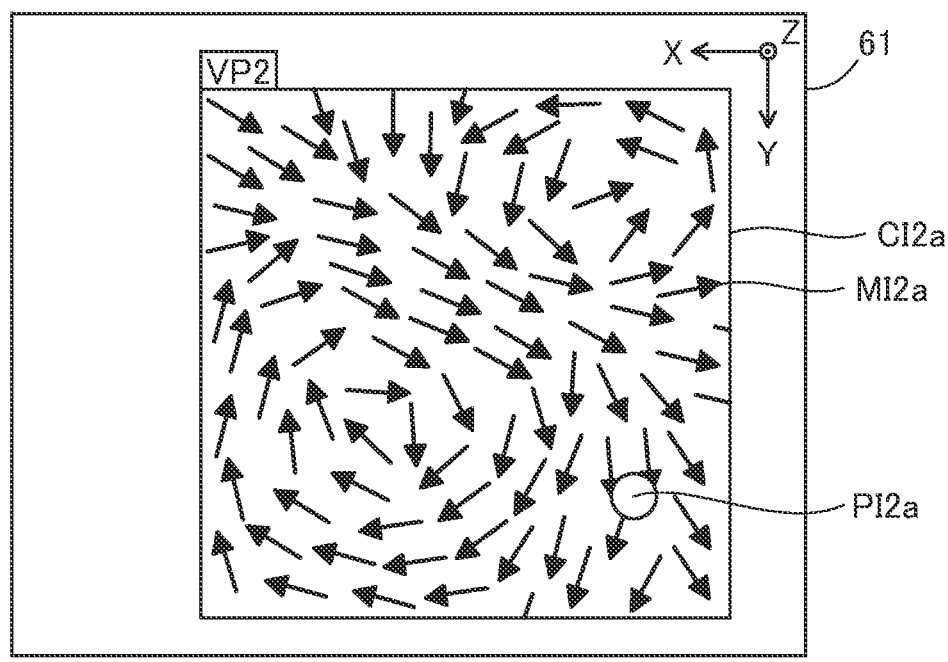
FIG. 17 is an explanatory diagram illustrating a display example of a combined image in a fifth embodiment.

FIG. 17 is an explanatory diagram illustrating a display example of the combined image CI in a fifth embodiment. The display example of the fifth embodiment is different from the display examples of the first embodiment regarding a mode of the biomagnetic field distribution image MI. Other parts of the configuration are similar to those of the first embodiment, and thus, description thereof will be omitted. In the biomagnetic field distribution image MI2 (FIGS. 9A and 9B) of the first embodiment, it is assumed that the biomagnetic field MFh is expressed by contour lines. In a biomagnetic field distribution image MI2a of the fifth embodiment, the biomagnetic field MFh is expressed by a plurality of arrows.

As illustrated in FIG. 17, a combined image CI2a corresponding to the second virtual plane VP2 is displayed on the display screen 61. The combined image CI2a includes the biomagnetic field distribution image MI2a and the catheter position image PI2a. In the biomagnetic field distribution image MI2a, a strength and orientation of the biomagnetic field MFh at each position of the second virtual plane VP2 is expressed by a length direction of the arrows. Similarly to the catheter position image PI2a of the third embodiment, the catheter position image PI2a has the shape of a white circle, and is displayed in an overlapping manner on the plurality of arrows of the biomagnetic field distribution image MI2a. A position of the catheter position image PI2a relative to the biomagnetic field distribution image MI2a indicates the position of the distal end portion of the catheter 20 relative to the biomagnetic field distribution.

According to the display example of the combined image CI of the present embodiment described above, the mode of the biomagnetic field distribution image MI is not limited to the shape of contour lines, and any mode can be adopted. Even in this case, the combined image CI includes the biomagnetic field distribution image MI expressing the strength of the biomagnetic field and the catheter position image PI expressing the position of the catheter 20, and thus, an operator of the catheter 20 can perform treatment while confirming the position of the distal end portion of the catheter 20 relative to the biomagnetic field distribution. Therefore, it is possible to improve the convenience during treatment.

Sixth Embodiment

Figure 18:
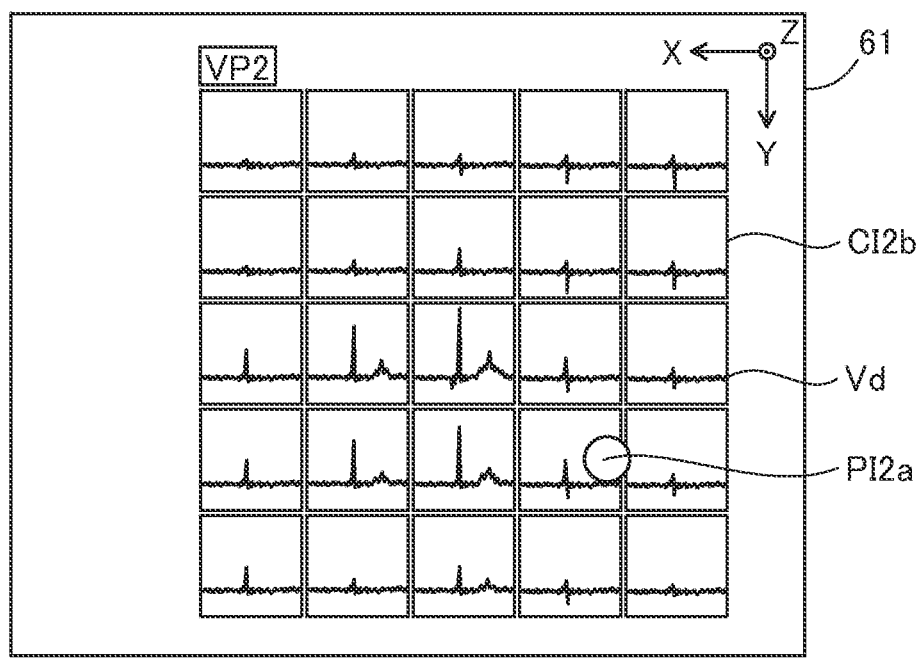
FIG. 18 is an explanatory diagram illustrating a display example of a combined image in a sixth embodiment.

FIG. 18 is an explanatory diagram illustrating a display example of the combined image CI in a sixth embodiment. The display example of the sixth embodiment is different from the display examples of the first embodiment regarding the method of displaying the strength of the biomagnetic field (cardiac magnetic field) MFh. Other parts of the configuration are similar to those of the first embodiment, and thus, description thereof will be omitted. In the first embodiment, the strength of the biomagnetic field MFh is expressed by the biomagnetic field distribution image MI. In the sixth embodiment, the detection value Vd of each of the magnetic sensors 11 at each position in a two-dimensional plane (XY plane) is displayed as an image expressing the strength of the biomagnetic field MFh.

As illustrated in FIG. 18, a combined image CI2b corresponding to the second virtual plane VP2 is displayed on the display screen 61. The combined image CI2b includes the detection value Vd of each of the magnetic sensors 11 and the catheter position image PI2a. The displayed detection value Vd of each of the magnetic sensors 11 is indicated by a polygonal line illustrating a time-series change of the strength of the biomagnetic field MFh at each position of the second virtual plane VP2. Similarly to the catheter position image PI2a of the third embodiment, the catheter position image PI2a has the shape of a white circle, and is displayed in an overlapping manner on an image of the detection value Vd. A position of the catheter position image PI2a relative to a display position of the detection value Vd of each of the magnetic sensors 11 indicates the position of the distal end portion of the catheter 20 relative to the biomagnetic field distribution.

According to the display example of the combined image CI of the present embodiment described above, the image included in the combined image CI and illustrating the strength of the biomagnetic field (cardiac magnetic field) MFh is not limited to the biomagnetic field distribution image MI, and any image can be adopted. Even in the present embodiment, the combined image CI includes an image expressing the strength of the biomagnetic field (the detection value Vd) and the catheter position image PI expressing the position of the catheter 20, and thus, an operator of the catheter 20 can confirm the position of the distal end portion of the catheter 20 relative to the biomagnetic field distribution. Therefore, it is possible to improve the convenience during treatment.

Modification of Present Embodiment

The disclosed embodiments are not limited to the above-described embodiments, and may be implemented in various modes without departing from the spirit of the disclosed embodiments. The following modifications can be applied, for example.

First Modification

Above, the treatment system 1 of the present embodiment is described when being used for an arrhythmia treatment. However, the treatment system 1 may be used for a treatment other than the arrhythmia treatment. Further, the treatment system 1 may be used for a treatment of an organ other than the heart. For example, the treatment system 1 may be used for a treatment of the brain. In this case, the magnetic sensor array 10 may have the shape of a hat worn by the human body 90 to be treated.

Second Modification

Above, the catheter 20 of the present embodiment is described as an ablation catheter using a plasma. However, in addition to the method of generating a plasma, the ablation method of the catheter 20 may be a method of passing a high frequency current, or a method of performing irradiation by a laser. Further, the method is not limited to the ablation method, and may include a method of injecting a drug via a puncture.

Third Modification

In the catheter 20 of the present embodiment above, the marker 24 and the distal tip 22 are formed separately. However, the marker 24 and the distal tip 22 do not need to be formed separately. For example, the distal tip 22 may be provided with a marker function by alternately passing a high frequency current for ablation and a current for position detection through the distal tip 22. Further, the treatment system 1 of the present embodiment is provided with the catheter 20, but a medical device such as a guide wire, an endoscope, and a dilator may be provided instead of the catheter 20. In this case, it is possible to use the combined image CI to display a position of a distal end portion of the medical device relative to the biomagnetic field distribution.

Fourth Modification

Above, the catheter 20 of the present embodiment is described in a configuration that uses a magnetic field generated by passing a current through a coil as the marker 24. However, if a permanent magnet is used as the marker 24, it is possible to eliminate the need for an operation of passing a current through the coil of the marker 24 in order to confirm the position of the distal end of the catheter 20. Further, if the marker 24 is a permanent magnet, a strength of the magnetic field generated by the permanent magnet is constant. Thus, if a difference between the strength of the magnetic field detected by the magnetic sensor array 10 and the strength of the magnetic field generated by the permanent magnet is determined, it is possible to determine a strength of the magnetic field originally generated by the living body. However, if the permanent magnet is used as the marker 24 and the strength of the magnetic field generated by the permanent magnet is much stronger than the strength of the magnetic field generated by the living tissue, it is difficult to appropriately detect, by the magnetic sensor array 10, the magnetic field generated by the living tissue. Therefore, it is desirable that the strength of the magnetic field generated by the permanent magnet is not more than 100 times the strength of the magnetic field generated by the living tissue.

Fifth Modification

In the combined image CI of the first to fifth embodiments, it is assumed that the catheter position image PI is displayed on the biomagnetic field distribution image MI. However, in the combined image CI, the biomagnetic field distribution image MI and the catheter position image PI may be displayed separately. Further, the biomagnetic field distribution image MI and the catheter position image PI may each be displayed in different display areas on the display screen 61.

Sixth Modification

It is assumed that the display screen 61 of the present embodiment displays the combined images CI corresponding to a plurality of the virtual planes VP that are parallel to each other. However, in addition to the combined images CI corresponding to the plurality of virtual planes VP parallel to each other, the combined images CI displayed on the display screen 61 may also be the combined images CI corresponding to a plurality of the virtual planes VP intersecting each other. That is, the combined images CI may not only include the combined images CI corresponding to the XY plane, but may also include the combined image CI corresponding to the virtual plane VP intersecting the XY plane, in accordance with an operation of the operating portion 70.

Seventh Modification

In the combined images CI of the present embodiment, a mode of the catheter position image PI changes depending on differences in the positions of the corresponding virtual planes VP in a Z-axis direction. However, in the combined image CI, the mode of the catheter position image PI may not change and remain constant, even if the position of the corresponding virtual plane VP in the Z-axis direction changes. Further, the shape of the catheter position image PI may be appropriately switchable, in accordance with an operation of the operating portion 70. Further, it is assumed that the combined image CI of the present embodiment includes one catheter position image PI corresponding to the distal end portion of the one catheter 20. However, the combined image CI may include a plurality of the catheter position images PI corresponding to each of distal end portions of a plurality of catheters. In this case, only the catheter position image PI corresponding to a selected catheter may be displayed from among the plurality of catheter position images PI, by an operation of the operating portion 70. That is, the catheter for which the catheter position image PI is displayed may be switched by the operation of the operating portion 70. Further, the shapes of the plurality of catheter position images PI may be different from each other.

Eighth Modification

A content of the biomagnetic field distribution image MI described in the present embodiment is only an example, and the content of the biomagnetic field distribution image MI is not limited to the content of the above embodiment. For example, in the biomagnetic field distribution image MI of the above embodiment, the strength of the biomagnetic field MFh is expressed by contour lines. However, the strength of the biomagnetic field MFh may be expressed by a numerical value, or may be expressed by a line graph. Further, the orientation of the biomagnetic field MFh may be expressed by a triangle, a symbol, or the like. Moreover, instead of the biomagnetic field distribution image MI, an image illustrating the flow or the density of a current generated by the living body may be used. Even in this case, the image illustrating the flow or the density of the current generated by the living body can be said to be an image illustrating the strength of a biomagnetic field.

Ninth Modification

The display example of the display screen 61 of the present embodiment is only an example, and a display content may be different from the display example described above. A part of the display example described above may not be displayed, or another image may be added. For example, the legend EN may not be displayed, or the blood pressure or an image of an operating portion may be displayed.

Tenth Modification

The configuration of the present embodiment can also be applied to a device other than a treatment system. For example, the configuration of the present embodiment can also be applied to an examination system, an examination method, an image generation device, an image generation method, and the like. Further, in each of the configurations of the treatment systems described in the first to sixth embodiments, parts of the configurations can be appropriately combined and a part of the configuration can be omitted where appropriate.

Although the aspects have been described based on the embodiments and the modifications, the embodiments of the above-described aspects are for facilitating understanding of the aspects, and do not limit the aspects. The aspects can be modified and improved without departing from the spirit of the aspects and the scope of the claims, and equivalent aspects are included in the aspects. Further, unless a technical feature is described as essential in the present specification, it may be omitted as appropriate.

DESCRIPTION OF REFERENCE NUMERALS

1 . . . Treatment system
10 . . . Magnetic sensor array
20 . . . Catheter
22 . . . Distal tip
24 . . . Marker
30 . . . High frequency generator
40 . . . Position detection portion
50 . . . Computer
51 . . . Main control portion
52 . . . Image information processing portion
521 . . . Magnetic distribution image generation portion
522 . . . Position image generation portion
523 . . . Combined image generation portion
60 . . . Monitor
61 . . . Display screen
70 . . . Operating portion
90 . . . Human body
91 . . . Heart
CI . . . Combined image
PI . . . Catheter position image
MI . . . Biomagnetic field distribution image
SI . . . Heart model image
FI . . . Heart rate display image
VP . . . Virtual plane
DMI . . . Combined magnetic field distribution image
MFh . . . Biomagnetic field
MFm . . . Marker magnetic field

The invention claimed is:

1. A treatment system comprising:
a magnetic sensor configured to detect a biomagnetic field generated by a living body to be treated;
a catheter configured to be inserted into the living body;
an image information processor programmed to generate a combined image including a first image expressing a strength of the biomagnetic field and a second image expressing a position of the catheter, by using biomagnetic field information output from the magnetic sensor and position information of the catheter inserted into the living body; and
a display configured to display the combined image.

2. The treatment system according to claim 1, wherein the first image expresses a biomagnetic field distribution that is a distribution of the biomagnetic field generated by a specific organ of the living body, and the second image indicates a position of a distal end portion of the catheter relative to the biomagnetic field distribution.

3. The treatment system according to claim 2, wherein the second image further indicates an orientation of the distal end portion of the catheter relative to the biomagnetic field distribution.

4. The treatment system according to claim 3, wherein the display displays first and second combined images as two of the combined images,
the first combined image expresses the biomagnetic field distribution at a first position of the specific organ and indicates the position of the distal end portion of the catheter relative to the biomagnetic field distribution at the first position, and
the second combined image expresses the biomagnetic field distribution at a second, different position of the specific organ and indicates the position of the distal end portion of the catheter relative to the biomagnetic field distribution at the second position.

5. The treatment system according to claim 4, further comprising:
an operating device configured to change a content of the combined image displayed on the display, wherein
in response to the operating device receiving an operation, the image information processor uses the biomagnetic field information to generate a new combined image expressing a new biomagnetic field distribution at a new position of the biomagnetic field generated by the specific organ corresponding to the operation, and indicating the position of the distal end portion of the catheter relative to the new biomagnetic field distribution.

6. The treatment system according to claim 3, further comprising:
an operating device configured to change a content of the combined image displayed on the display, wherein
in response to the operating device receiving an operation, the image information processor uses the biomagnetic field information to generate a new combined image expressing a new biomagnetic field distribution at a new position of the biomagnetic field generated by the specific organ corresponding to the operation, and indicating the position of the distal end portion of the catheter relative to the new biomagnetic field distribution.

7. The treatment system according to claim 3, wherein the catheter includes a marker at the distal end portion,
the magnetic sensor is further configured to detect a magnetic field generated by the marker, and
the image information processor generates the combined image by using magnetic field information including position information of the marker output from the magnetic sensor and the biomagnetic field information.

8. The treatment system according to claim 2, wherein the display displays first and second combined images as two of the combined images,
the first combined image expresses the biomagnetic field distribution at a first position of the specific organ and indicates the position of the distal end portion of the catheter relative to the biomagnetic field distribution at the first position, and
the second combined image expresses the biomagnetic field distribution at a second, different position of the specific organ and indicates the position of the distal end portion of the catheter relative to the biomagnetic field distribution at the second position.

9. The treatment system according to claim 8, further comprising:
an operating device configured to change a content of the combined image displayed on the display, wherein in response to the operating device receiving an operation, the image information processor uses the biomagnetic field information to generate a new combined image expressing a new biomagnetic field distribution at a new position of the biomagnetic field generated by the specific organ corresponding to the operation, and indicating the position of the distal end portion of the catheter relative to the new biomagnetic field distribution.

10. The treatment system according to claim 8, wherein the catheter includes a marker at the distal end portion, the magnetic sensor is further configured to detect a magnetic field generated by the marker, and the image information processor generates the combined image by using magnetic field information including position information of the marker output from the magnetic sensor and the biomagnetic field information.

11. The treatment system according to claim 2, wherein the catheter includes a marker at the distal end portion, the magnetic sensor is further configured to detect a magnetic field generated by the marker, and the image information processor generates the combined image by using magnetic field information including position information of the marker output from the magnetic sensor and the biomagnetic field information.

12. The treatment system according to claim 2, further comprising:
an operating device configured to change a content of the combined image displayed on the display, wherein
in response to the operating device receiving an operation, the image information processor uses the biomagnetic field information to generate a new combined image expressing a new biomagnetic field distribution at a new position of the biomagnetic field generated by the specific organ corresponding to the operation, and indicating the position of the distal end portion of the catheter relative to the new biomagnetic field distribution.

13. The treatment system according to claim 1, wherein the catheter includes a marker at a distal end portion, the magnetic sensor is further configured to detect a magnetic field generated by the marker, and the image information processor generates the combined image by using magnetic field information including position information of the marker output from the magnetic sensor and the biomagnetic field information.

14. The treatment system according to claim 1, wherein the magnetic sensor is formed in a sheet-like shape and is placed on a table where the living body to be treated lies.

15. The treatment system according to claim 1, wherein a position of the magnetic sensor relative to the living body to be treated is fixed.

16. The treatment system according to claim 1, wherein the catheter includes a marker at a distal end portion of the catheter, the marker is configured to generate a magnetic field by supply of a current for position detection, the magnetic sensor is further configured to detect a magnetic field generated by the marker, and the image information processor is configured to generate the combined image by using magnetic field information including position information of the marker output from the magnetic sensor and the biomagnetic field information.

17. An image generation method comprising:
detecting a biomagnetic field generated by a living body to be treated; and
generating a combined image including a first image expressing a strength of the biomagnetic field and a second image expressing a position of a catheter inserted into the living body, by using biomagnetic field information relating to the detected biomagnetic field and position information of the catheter.

18. The image generation method according to claim 17, wherein
the biomagnetic field is detected by a magnetic sensor that is formed in a sheet-like shape and is placed on a table where the living body to be treated lies.

19. The image generation method according to claim 17, wherein
the biomagnetic field is detected by a magnetic sensor, and a position of the magnetic sensor relative to the living body to be treated is fixed.

20. The image generation method according to claim 17, wherein
the biomagnetic field is detected by a magnetic sensor, and
the catheter includes a marker at a distal end portion of the catheter, the marker is configured to generate a magnetic field by supply of a current for position detection, the magnetic sensor is further configured to detect a magnetic field generated by the marker, and the combined image is generated by using magnetic field information including position information of the marker output from the magnetic sensor and the biomagnetic field information.

\* \* \* \* \*